US012162807B2

United States Patent
McEntire et al.

(10) Patent No.: US 12,162,807 B2
(45) Date of Patent: Dec. 10, 2024

(54) METHODS OF SURFACE FUNCTIONALIZATION OF ZIRCONIA-TOUGHENED ALUMINA WITH SILICON NITRIDE

(71) Applicant: SINTX TECHNOLOGIES, INC., Salt Lake City, UT (US)

(72) Inventors: Bryan J. McEntire, Salt Lake City, UT (US); Bhajanjit Singh Bal, Salt Lake City, UT (US); Ryan M. Bock, Salt Lake City, UT (US)

(73) Assignee: SINTX Technologies, Inc., Salt Lake City, UT (US)

( * ) Notice: Subject to any disclaimer, the term of this patent is extended or adjusted under 35 U.S.C. 154(b) by 116 days.

(21) Appl. No.: 17/634,141

(22) PCT Filed: Jun. 11, 2020

(86) PCT No.: PCT/US2020/037170
§ 371 (c)(1),
(2) Date: Feb. 9, 2022

(87) PCT Pub. No.: WO2021/034385
PCT Pub. Date: Feb. 25, 2021

(65) Prior Publication Data
US 2022/0289637 A1 Sep. 15, 2022

(51) Int. Cl.
*C04B 41/00* (2006.01)
*A61F 2/30* (2006.01)
(Continued)

(52) U.S. Cl.
CPC ........ *C04B 41/0036* (2013.01); *A61F 2/3094* (2013.01); *B23K 26/0006* (2013.01); *B23K 26/0622* (2015.10); *B23K 26/342* (2015.10); *C04B 35/10* (2013.01); *C04B 41/0072* (2013.01); *C04B 41/4545* (2013.01); *C04B 41/5022* (2013.01); *C04B 41/5066* (2013.01); *C04B 41/5346* (2013.01);
(Continued)

(58) Field of Classification Search
CPC .......................... C04B 41/0036; A61L 27/306
See application file for complete search history.

(56) References Cited

U.S. PATENT DOCUMENTS

| 2010/0016987 | A1* | 1/2010 | Scrafton | ............... A61L 27/306 427/2.27 |
| 2014/0277571 | A1 | 9/2014 | Pettersson et al. | |

(Continued)

FOREIGN PATENT DOCUMENTS

GB  2025238 A  1/1980

OTHER PUBLICATIONS

Marin et al., Bioglass functionalization of laser-patterned bioceramic surfaces and their enhanced bioactivity, 2018, Heliyon, vol. 4, pp. 1-24 (Year: 2018).*

(Continued)

*Primary Examiner* — Dah-Wei D. Yuan
*Assistant Examiner* — Andrew J Bowman
(74) *Attorney, Agent, or Firm* — Polsinelli PC

(57) ABSTRACT

Disclosed herein are methods for functionalizing the surface of a biomedical implant. The biomedical implant may be a zirconia-toughened alumina implant surface functionalized with silicon nitride powder for promoting osteogenesis.

18 Claims, 22 Drawing Sheets

(51) Int. Cl.
  B23K 26/00    (2014.01)
  B23K 26/0622  (2014.01)
  B23K 26/342   (2014.01)
  C04B 35/10    (2006.01)
  C04B 41/45    (2006.01)
  C04B 41/50    (2006.01)
  C04B 41/53    (2006.01)
  C04B 41/87    (2006.01)
  C04B 41/91    (2006.01)
  B23K 103/00   (2006.01)

(52) U.S. Cl.
  CPC .............. *C04B 41/87* (2013.01); *C04B 41/91*
      (2013.01); *A61F 2002/30807* (2013.01); *A61F*
      *2002/3097* (2013.01); *A61F 2310/00203*
      (2013.01); *A61F 2310/00239* (2013.01); *A61F*
      *2310/00874* (2013.01); *B23K 2103/52*
      (2018.08); *C04B 2235/3217* (2013.01); *C04B*
      *2235/3244* (2013.01)

(56) References Cited

U.S. PATENT DOCUMENTS

| 2016/0339144 | A1 | 11/2016 | McEntire et al. |
| 2017/0197014 | A1 | 7/2017  | McEntire et al. |
| 2018/0243097 | A1 | 8/2018  | Jones et al.    |
| 2020/0197565 | A1 | 6/2020  | Suh et al.      |

OTHER PUBLICATIONS

Japan Patent Office, Notice of Reasons for Rejection, Application No. 2022-511396, 10 pages.

Office Action issued Aug. 22, 2022 in Chinese Patent Application No. 202080057087.X, 15 pages.

Marin et al., Bioglass functionalization of laser-patterned bioceramic surfaces and their enhanced bioactivity, Heliyon, 24 pages, 2018.

Xu et al., Laser Cladding of Composite Bioceramic Coatings on Titanium Alloy, JMEPEG (2016) 25:656-667, 12 pages, 2016.

McEntire et al., Processing and Characterization of Silicon Nitride Bioceramics, Bioceramics Development and Applications, 9 pages, 2016.

Indian Patent Office, First Examination Report, Indian Patent Application No. 202217002063, dated Jan. 2, 2023, 12 pages.

Canadian Intellectual Property Office, Official Action, Application No. 3,147,286, Aug. 8, 2023, 4 pages.

China National Intellectual Property Adminstration, Third Office Action, Application No. 202080057087.X, May 9, 2023, 14 pages.

China National Intellectual Property Administration, Decision of Rejection, Application No. 202080057087.X, dated Aug. 23, 2023, 13 pages.

China National Intellectual Property Adminstration, Second Office Action, Application No. 202080057087.X, Feb. 9, 2023, 13 pages.

International Search Report and Written Opinion issued in corresponding Application No. PCT/US2020/037170 on Sep. 21, 2020, 12 pages.

Marin et al., Bioglass functionalization of laser-patterned bioceramic surfaces and their enhances bioactivity, Heliyon vol. 4, Issue 2 (Dec. 2018), pp. 1-24.

Zanocco et al., 3D-additive deposition of an antibacterial and osteogenic silicon nitride coating on orthopaedic titanium substrate, Journal of the Mechanical Behavior of Biomedical Materials, vol. 103 (Nov. 26, 2019), pp. 1-11.

Marin et al., Silicon nitride laser cladding: A feasible technique to improve the biological response of zirconia, Materials & Design, vol. 191 (Mar. 17, 2020) pp. 1-12.

Marin et al., Enhanced bioactivity of Si3N4 through trench-patterning and back-filling with bioglass, Materials Science & Engineering C, vol. 106 (Oct. 7, 2019), pp. 1-10.

European Patent Office, Extended European Search Report, Application No. 20854278.7, May 22, 2023, 9 pages.

IP Australia, Examination Report No. 1 Standard Patent Application, Application No. 202334770, Jun. 20, 2023, 5 pages.

European Patent Office, Extended European Search Report, Application No. 23216848.4, Apr. 25, 2024, 9 pages.

\* cited by examiner

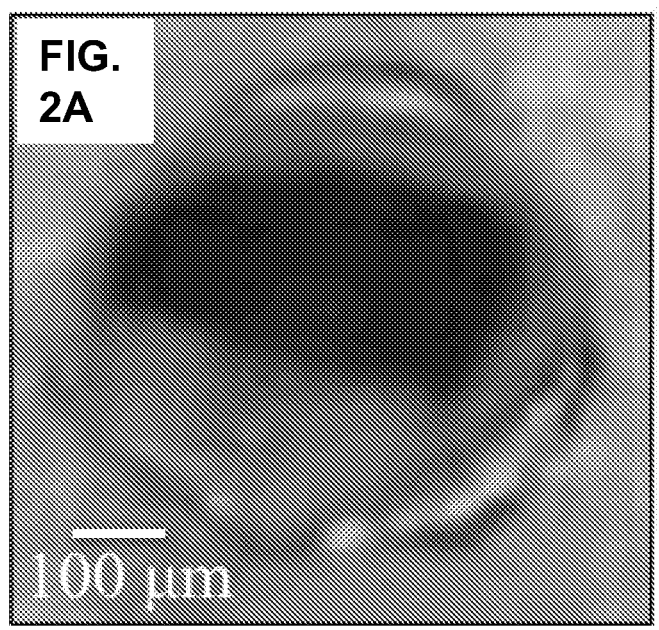
FIG. 2A
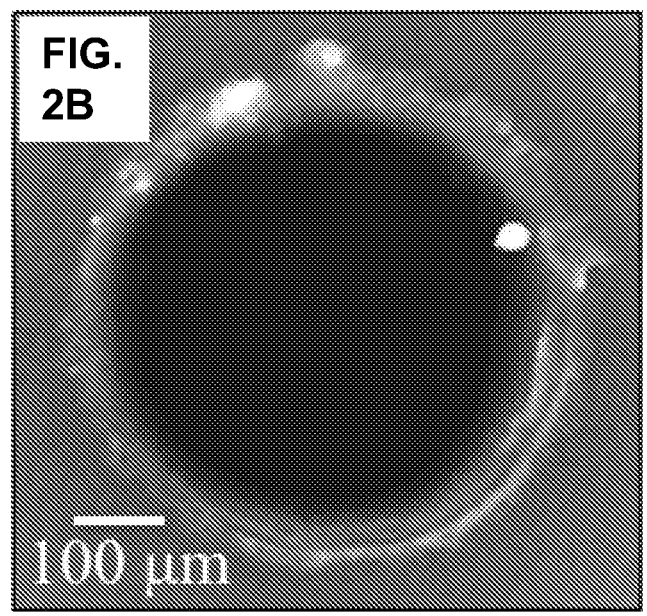
FIG. 2B
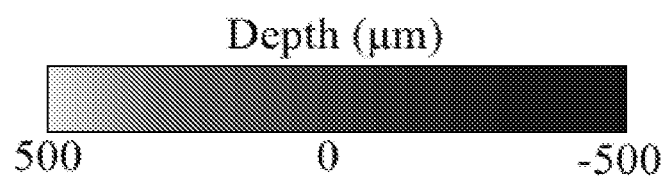

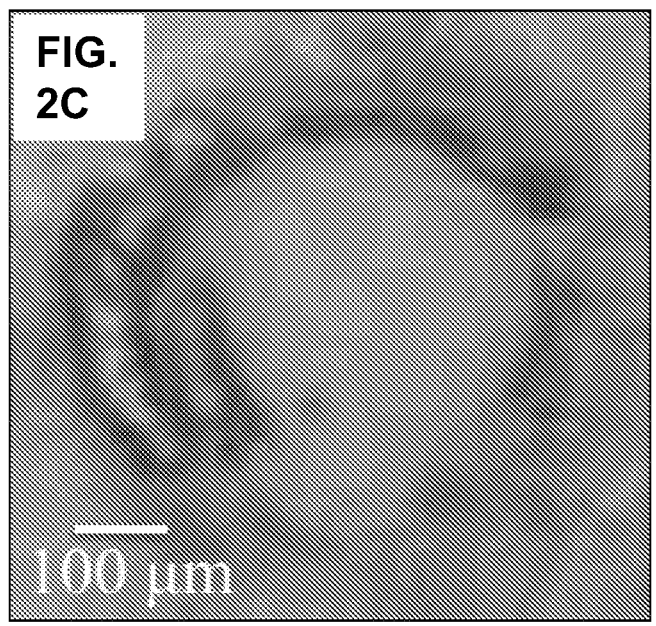
FIG. 2C
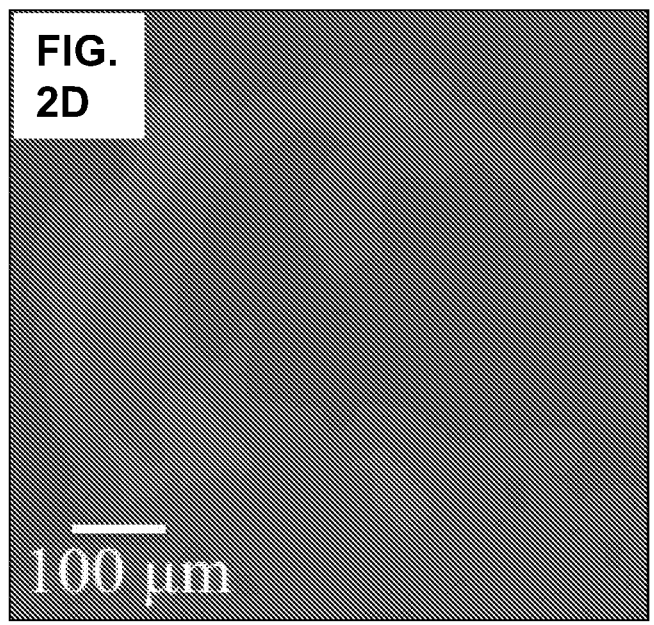
FIG. 2D
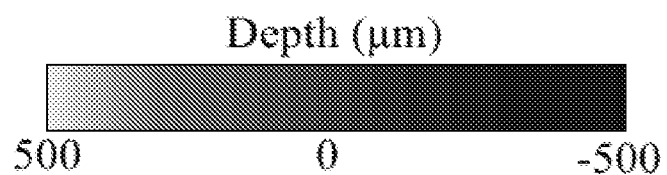
Depth (μm)

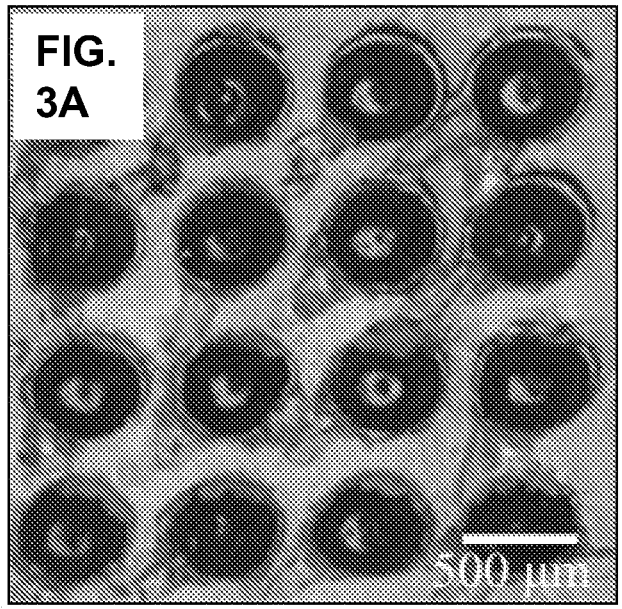
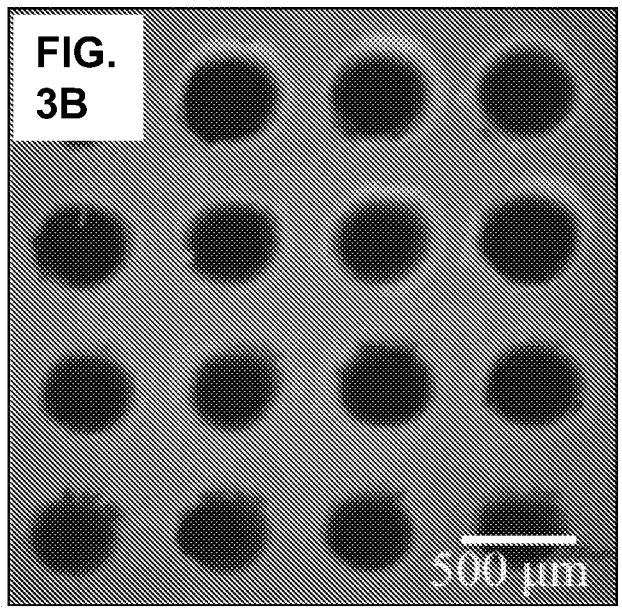
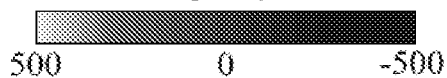
Depth (μm)
500   0   -500

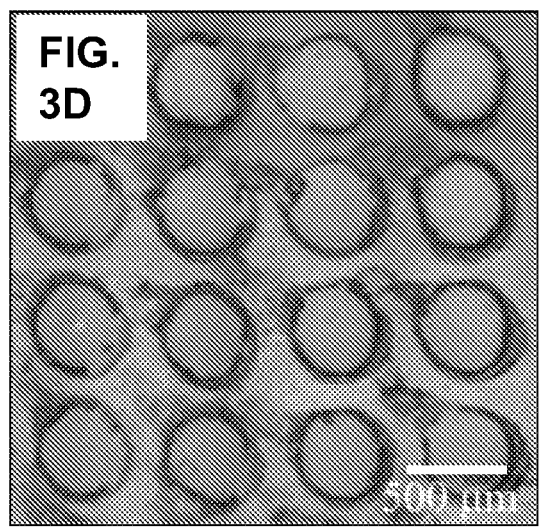
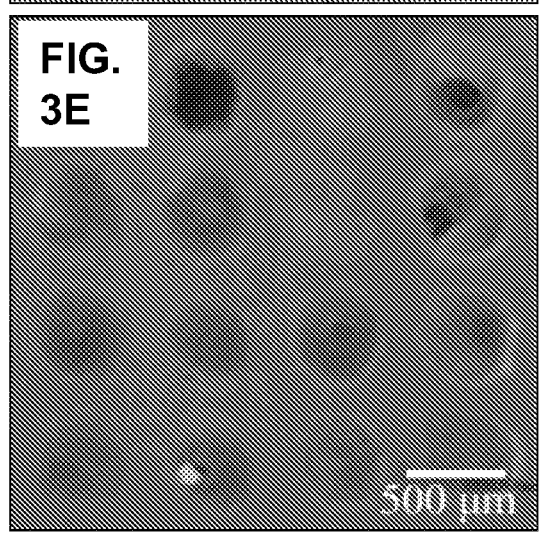
Depth (μm)
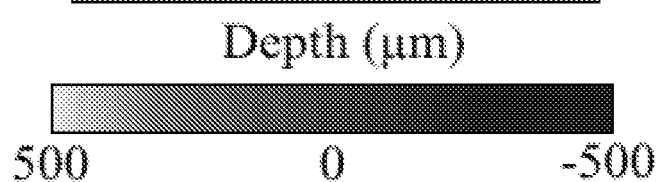

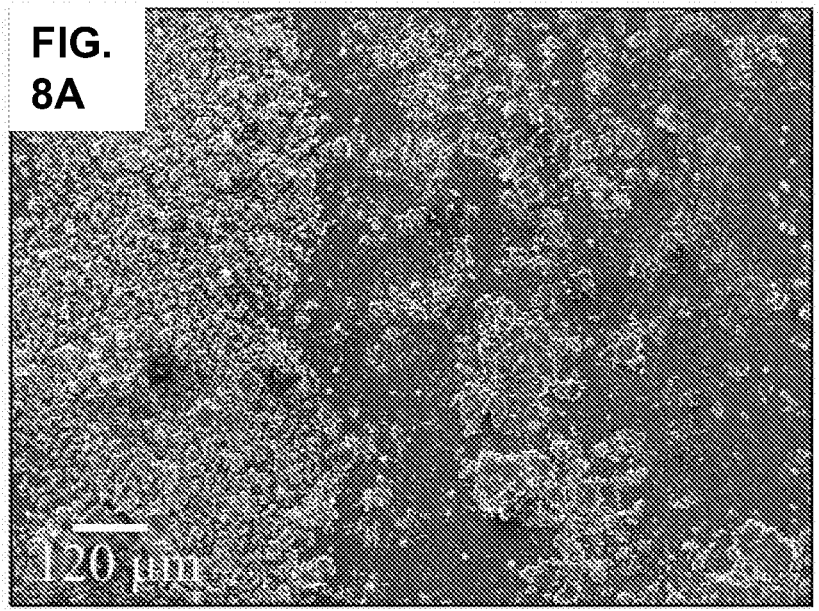
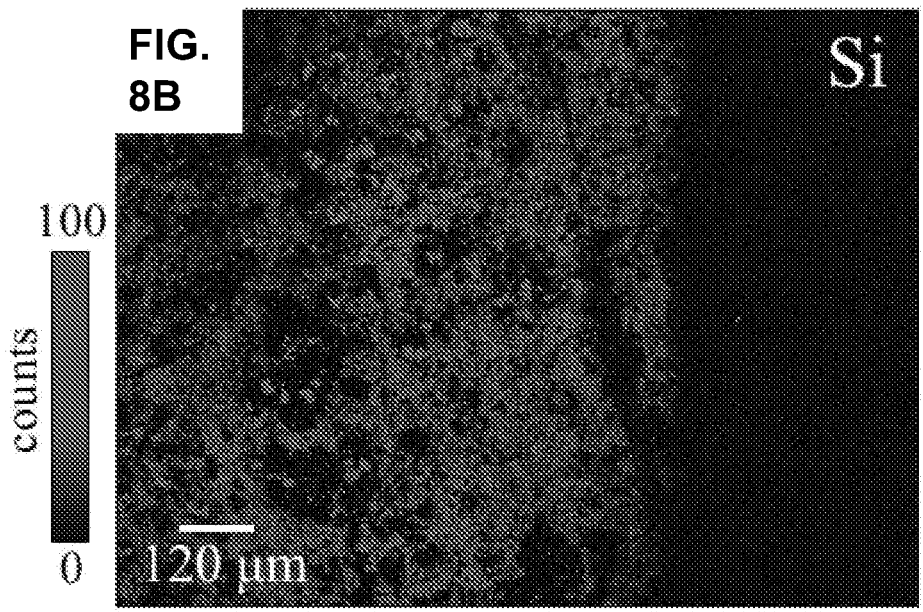

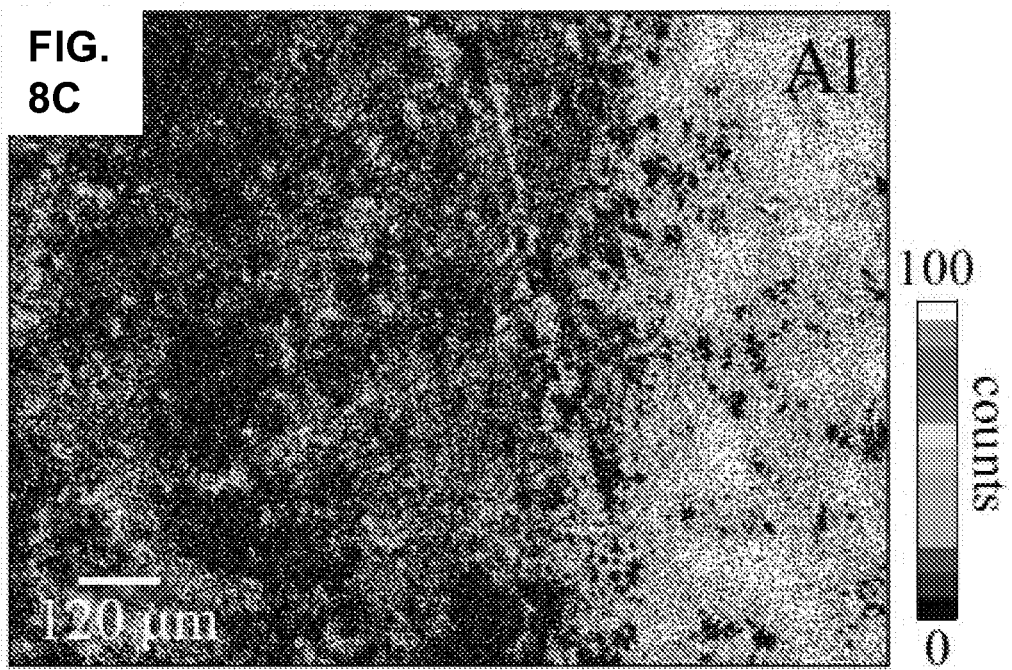
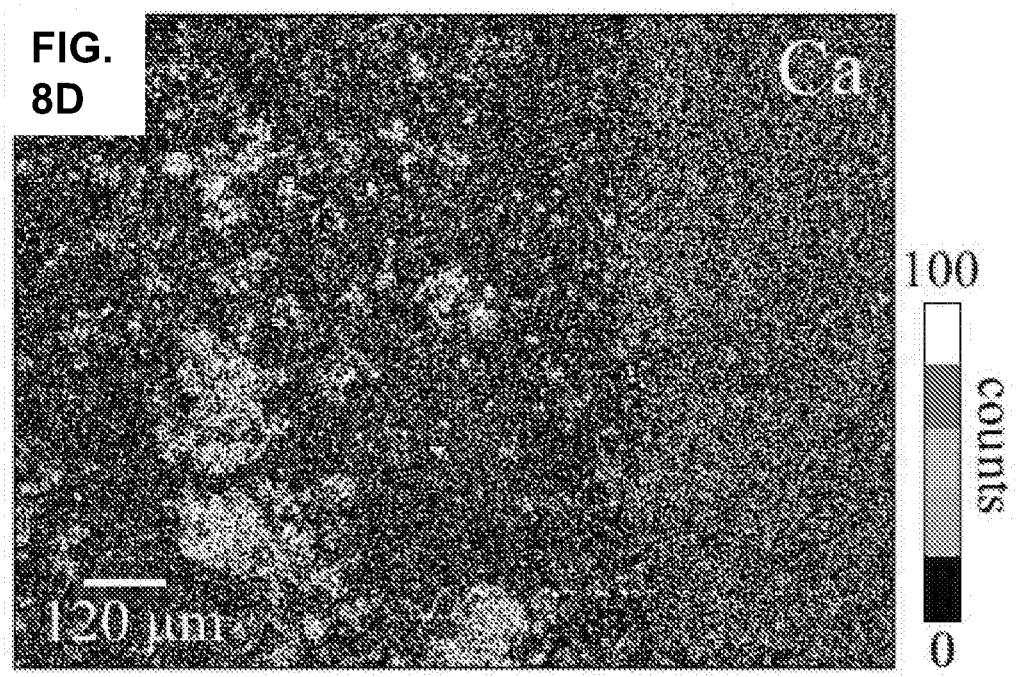

METHODS OF SURFACE FUNCTIONALIZATION OF ZIRCONIA-TOUGHENED ALUMINA WITH SILICON NITRIDE

CROSS-REFERENCE TO RELATED APPLICATIONS

This application is a US national phase application of PCT application No. PCT/US2020/037170 filed on Jun. 11, 2020, which claims priority to U.S. Provisional Application No. 62/888,850, filed Aug. 19, 2019, which are hereby incorporated herein by reference in their entirety.

FIELD

The present disclosure relates to methods of surface functionalization of biomedical implants with silicon nitride. More specifically, the disclosure relates to promoting osteogenesis using zirconia-toughened alumina implants surface functionalized with silicon nitride.

BACKGROUND

During bone formation, organic matrix (i.e., predominantly collagen type I) is synthesized by cells secreting a variety of glycoproteins, genetic markers, and bone sialoprotein. A favorable environment for cellular apatite mineralization relies on local supersaturation of extra-cellular fluids with osteoblastic alkaline phosphatase (ALP), pyrophosphatase activity, and osteocalcin production. ALP increases phosphate concentration by cleaving phosphate groups; pyrophosphatase degrades pyrophosphate, which inhibits phosphate cleavage; and osteocalcin binds calcium. The surface chemistry of orthopaedic implants designed to promote bone formation at tissue/implant interface is thus an important consideration. Although ceramic materials are considered to be bioinert, they can in fact stimulate or suppress osteoblastic activity. For example, silicon nitride ($Si_3N_4$) implants are known to accelerate bone repair because of the surface chemistry of the material. The release of silicic acid and reactive nitrogen species (RNS) on $Si_3N_4$ surfaces enhances osteogenic activity in osteosarcoma and mesenchymal cells. Analyses of a retrieved $Si_3N_4$ human cervical fusion implant have confirmed the incorporation of silicon and nitrogen into the crystal lattice of native hydroxyapatite. Data have also shown that hydrolysis at $Si_3N_4$ surfaces releases Si and RNS ions that favor bone formation, while alumina ($Al_2O_3$) surfaces lead to the elution of $Al^{3+}$ and reactive oxygen species (ROS) instead. $Al^{3+}$ ions inhibit mineralization by slowing hydroxyapatite crystal formation and altering the influx and efflux of calcium from bone cells. Moreover, the formation of ROS leads to oxidative stress in cells with significant perturbation of their normal anti-oxidative system. In vivo and in vitro data have shown that $Al^{3+}$ and ROS-induced oxidative stress activates cell apoptotic signaling pathways. ROS cause damage to cell proteins, lipids, and DNA. It targets important regulator pathways for calcium and its intracellular receptor calmodulin. Ultimately, this leads to osteoblast apoptosis. Because of these properties, alumina-based orthopaedic implants are limited to low-wear applications, such as the bearings of prosthetic hip joints.

Therefore, there is a need for alternative bioceramics or surface functionalized bioceramics to reduce or eliminate the elution of $Al^{3+}$ and ROS, while promoting osteogenesis.

SUMMARY

In an aspect, the present disclosure encompasses a method of functionalizing the surface of a biomedical implant. The method may include providing the biomedical implant, directing a laser to a surface of the biomedical implant to produce a grid of equidistant, patterned wells, and filling the patterned wells with a powder mixture comprising a bioglass and silicon nitride. The silicon nitride may be present in the powder mixture at about 5 mol. % to about 10 mol. %. In some aspects, the biomedical implant is made zirconia-toughened alumina and surface functionalized with silicon nitride. In some embodiments, the silicon nitride is $\alpha$-$Si_3N_4$. In some aspects, the biomedical implant is made zirconia-toughened alumina and surface functionalized with silicon nitride. In one aspect, the patterned wells are a two dimensional feature extended into the surface of the implant and each of the patterned wells may be about 0.2 $mm^2$ in cross-section area with an interspace of about 1.0 mm. In some embodiments, the patterned wells may be a 4×4 grid. The bioglass may include 45 wt. % $SiO_2$, 24.5 wt. % CaO, 24.5 wt. % $Na_2O$, and 6 wt. % $P_2O_5$. In some embodiments, the powder mixture may include 5.5 wt. % to about 10.7 wt. % silicon nitride. In a further feature, the powder mixture may comprise 5.5 wt. % to about 10.7 wt. % silicon nitride. In addition, the method of filling the patterned wells may include pressing the powder mixture onto the biomedical implant surface, and removing the excess powder mixture. In yet another aspect, the method for includes forming the powder mixture by homogenizing and melting powder mixtures of the bioglass and silicon nitride in a platinum crucible in nitrogen gas atmosphere. In another embodiment, the laser may be a Nd:YAG laser having a wavelength of 1064 nm and wherein the laser may have a focusing distance of about 250 nm, a nominal maximum power of about 17 kW, a burst energy of about 70 joules, an applied potential of about 160-500 V, and/or a discharge time of about 1-20 ms.

Further provided herein is a method of functionalizing the surface of a biomedical implant that includes providing the biomedical implant, applying a layer of silicon nitride powder on a water-wet surface of the biomedical implant, pulsing a laser on the layer of silicon nitride to sinter the silicon nitride, and repeating the pulsing steps until the sintered silicon nitride layer has a thickness of about 10 μm to about 20 μm. In one embodiment, the biomedical implant comprises zirconia-toughened alumina and the silicon nitride is β-Si3N4 and the silicon nitride may be mixed with 6 wt. % yttrium oxide and 4 wt. % aluminum oxide. In some embodiments, the laser may be a Nd:YAG laser having a wavelength of 1064 nm and wherein the laser may have a nominal maximum power of about 17 kW, a maximum pulse energy of about 70 Joules, a voltage of about 400 V, a spot size of about 2 μm, and/or a pulse time of about 4 ms.

Also provided here are methods of promoting osteogenesis using a zirconia-toughened alumina implant surface functionalized with silicon nitride. In one aspect, osteoblast cell proliferation increases on the biomedical implant as compared to an implant without the silicon nitride powder mixture. In another aspect, osteoblast cell proliferation increases on the biomedical implant as compared to an implant without silicon nitride in the powder mixture. In some embodiments, area coverage and specific volume of biological tissue on the surface functionalization biomedical implant is at least 200% higher than that of an uncoated implant. In another embodiment, mineralized tissue increases on the biomedical implant as compared to an implant without the silicon nitride powder mixture. In one aspect, there may be an increase in mineral hydroxyapatite on the biomedical implant as compared to an implant without the silicon nitride powder mixture.

Other aspects and iterations of the invention are described more thoroughly below.

BRIEF DESCRIPTION OF THE DRAWINGS

The accompanying drawings, which are incorporated in and constitute a part of this specification, illustrate several embodiments of the invention and together with the description serve to explain the principles of the invention.

FIG. 2A is a high-magnification image of a laser-drilled well on the ZTA surface using optical microscopy; FIG. 2B is a high-magnification image of a laser-drilled well on the ZTA surface using laser topography; FIG. 2C is an optical image of the well after filling with Bioglass®/$Si_3N_4$ powder; and FIG. 2D is a laser image of the well after filling with Bioglass®/$Si_3N_4$ powder.

FIG. 3A is an optical micrograph of a 4×4 grid of wells 500 μm in diameter patterned on the ZTA surface; FIG. 3B is a laser micrograph of a 4×4 grid of wells 500 μm in diameter patterned on the ZTA surface; FIG. 3D is an optical image of the well grid after filling with Bioglass®/$Si_3N_4$ powder; and FIG. 3E is a laser image of the well grid after filling with Bioglass®/$Si_3N_4$ powder.

FIG. 8A is an SEM image of the same region shown in FIG. 7A after 1-week in vitro exposure to SaOS-2 osteoblasts in biological environment; FIG. 8B is an EDS map of Si collected in the same region shown in FIG. 7A after 1-week in vitro exposure to SaOS-2 osteoblasts in biological environment; FIG. 8C is Can EDS map of Al collected in the same region shown in FIG. 7A after 1-week in vitro exposure to SaOS-2 osteoblasts in biological environment; FIG. 8D is an EDS map of Ca collected in the same region shown in FIG. 7A after 1-week in vitro exposure to SaOS-2 osteoblasts in biological environment.

DETAILED DESCRIPTION

Figure 1A:
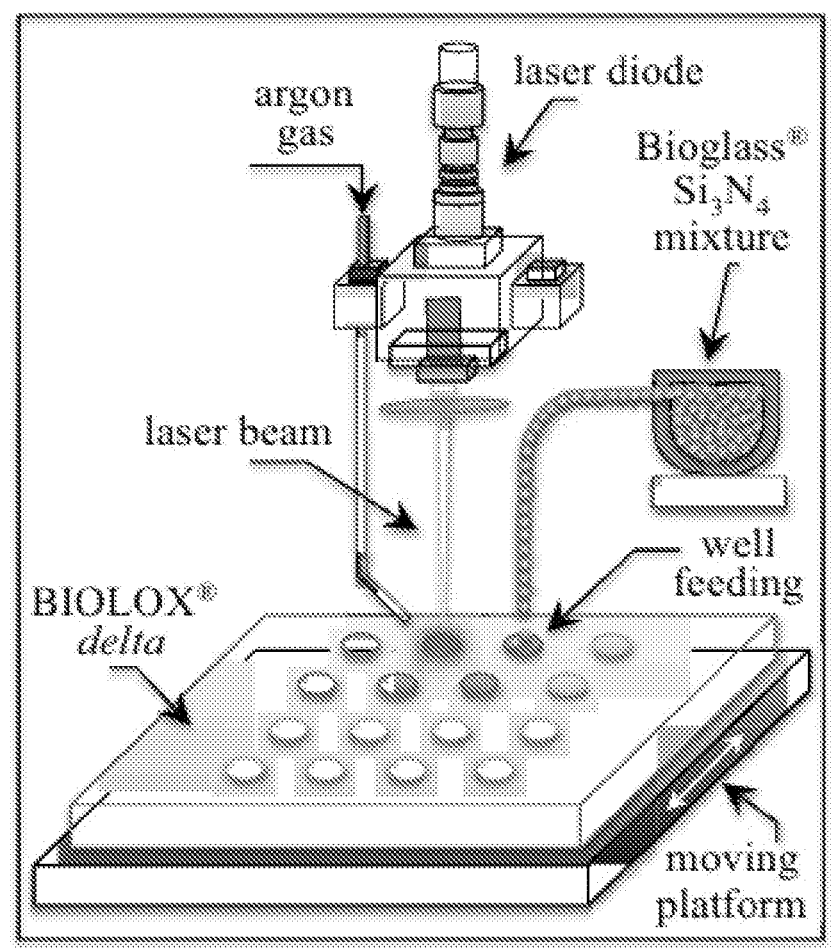
FIG. 1A is a schematic of surface laser patterning on ZTA substrate and filling of the patterned wells with powder mixtures of Bioglass® and $Si_3N_4$.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims or can be learned by the practice of the principles set forth herein.

Active cytoskeletal proteins allow osteoblasts to maintain their structural integrity and facilitate their attachment to synthetic surfaces. The synthesis of organic matrix (i.e., predominantly collagen type I) requires the cells secreting a variety of glycoproteins, genetic markers, and bone sialoprotein to lay down pre-mineralized bone matrix and promote its mineralization. The multiple functions concurrently exploited by osteoblasts in synthesizing bone tissue obey delicate equilibriums that are in turn strongly influenced by environmental conditions. A favorable environment for apatite mineralization by cells should also favor local supersaturation of extra-cellular fluids. The supersaturated extracellular environment is developed as a consequence of the concurrent increases in osteoblastic alkaline phosphatase (ALP), pyrophosphatase activity, and osteocalcin production to locally raise phosphate and calcium concentrations. ALP increases phosphate concentration by cleaving phosphate groups; pyrophosphatase degrades pyrophosphate, which inhibits phosphate cleavage; and osteocalcin binds calcium. The surface chemistry of a synthetic substrate to which cells are exposed in biological environment is crucial in regulating cell function and osteogenesis. The kinetics of ionic elution from the substrate surface can greatly affect ALP activity and osteocalcin production by cells. Therefore, substrate chemistry can be tailored to counteract bone resorption pathologies and to promote bone formation at tissue/implant interface.

Figure 10:
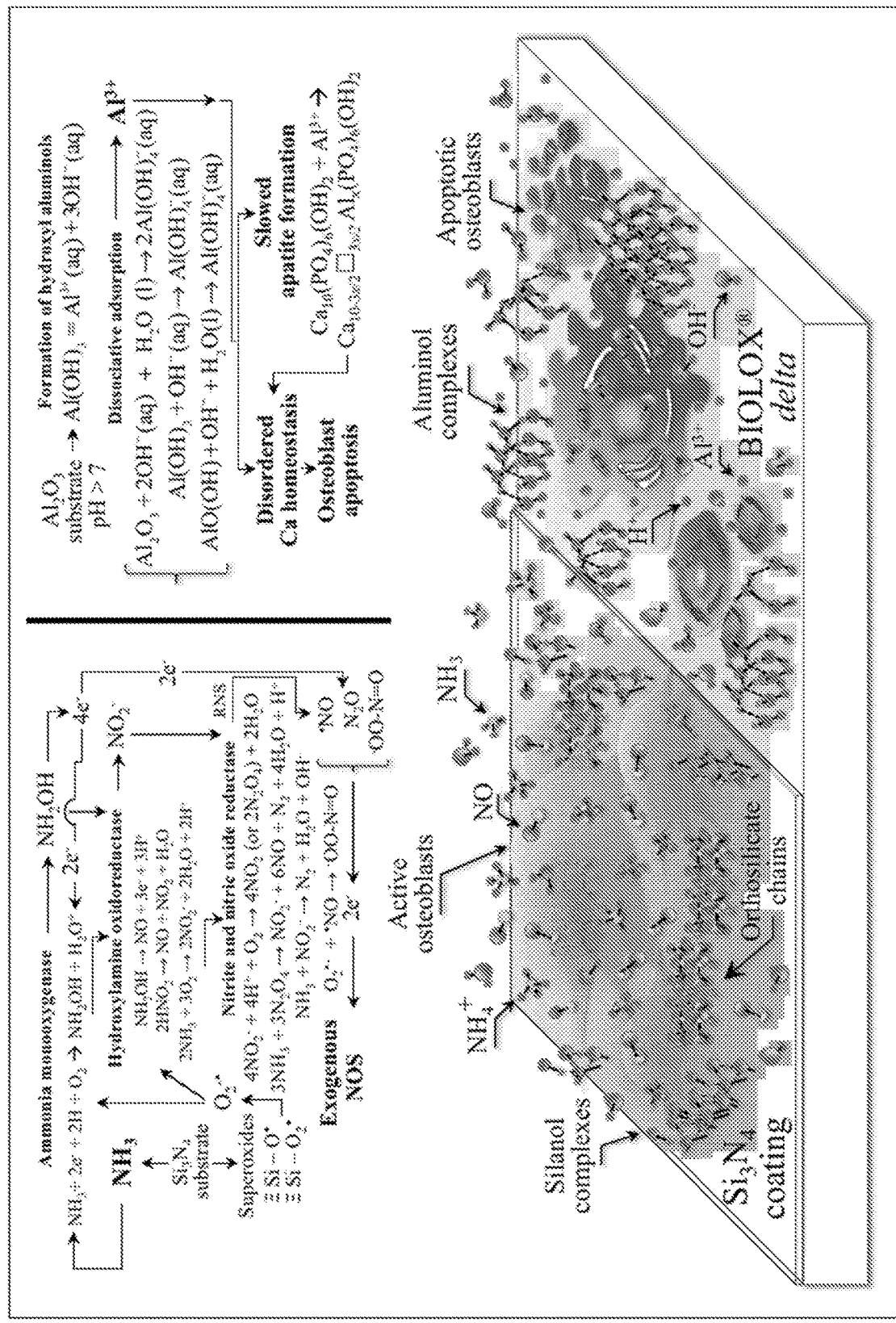
FIG. 10 shows a schematic of RNS- and silanol-based chemical interaction between $Si_3N_4$ substrate and proliferating human osteoblasts (left side) and ROS- and aluminol-based chemical interaction between BIOLOX®delta ZTA and apoptotic osteoblasts (right side). The square box in the chemical formula of hydroxyapatite modified by $Al^{3+}$ ions represents Ca vacancies.

As stated above, bioceramic implants that include alumina lead to elution of $Al^{3+}$ and ROS. From a biochemistry viewpoint, aluminum interferes with osteoid calcification by preventing the growth of calcium phosphate crystals. The localization of aluminum at the interface with the bone mineralization front shows that $Al^{3+}$ ions act as physicochemical inhibitors of calcification. $Al^{3+}$ cations can substitute for $Ca^{2+}$ in the structure of apatite. However, their presence "locks" the structure and inhibits further mineralization by slowing the rate of hydroxyapatite crystal formation, while also altering the influx and efflux of calcium from bone cells. FIG. 10 shows the interaction between a zirconia-toughened alumina (ZTA) surface (rich in $Al_2O_3$) and apoptotic osteoblasts. The off-stoichiometry equations governing the cell/ZTA-substrate interactions in aqueous environment, which are made explicit in the corresponding upper part of the figure, indicate elution of $Al^{3+}$ ions and formation of hydroxyl aluminols. The former species eventually become incorporated in the mineral structure of bone tissue according to the indicated chemical equation for the Al-modified apatite structure. Dissociative adsorption, which involves the transfer of charge from the $Al_2O_3$ cluster to hydroxyl, oxygen, and proton radicals, represents the most likely event because it is more energetically favorable than molecular adsorption, in which $H_2O$ donates its charge to the $Al_2O_3$ cluster. The consequent (exogenous) development of ROS at the biomolecular cell/substrate interface might irreversibly damage proteins and nucleic acids, and cause peroxidation of membrane lipids, ultimately leading to cell apoptosis. Therefore, the above chemical circumstances at the cell/substrate interface may lead to why no cell proliferation and conspicuous osteogenesis inhibition is observed on a non-functionalized ZTA surface.

Silicon nitride ($Si_3N_4$) possesses unique surface chemistry that accelerates bone repair. The release of silicic acid and reactive nitrogen species (RNS) from the surface of $Si_3N_4$ may enhance the osteogenic activity of osteosarcoma and mesenchymal cells both at the initial stages of cell differentiation and during subsequent bony apatite deposition. Both elemental silicon and nitrogen may be deposited into the crystal lattice of native hydroxyapatite by osteoblasts. These foreign elements may stimulate progenitor cell differentiation and osteoblastic activity, which may ultimately result in accelerated bone ingrowth.

Provided herein are silicon nitride surface functionalized biomedical implants, methods of functionalizing the surface of a biomedical implant with silicon nitride ($Si_3N_4$), and methods of promoting osteogenesis using the surface functionalized biomedical implant. The methods of surface functionalization include (i) surface laser patterning and successive filling of the patterned wells with powder mixtures of bioglass and $Si_3N_4$; and, (ii) deposition of a micrometer thick $Si_3N_4$ layer using an automatic 3D-additive laser-sintering procedure. Both these procedures aim at turning the unfavorable $Al^{3+}$/ROS surface chemistry of an oxide ZTA ceramic into the $Si^{4+}$/RNS favorable one, while conserving unaltered its bulk mechanical properties. In addition, silicon nitride possesses a unique surface chemistry which is biocompatible and provides a number of biomedical applications including concurrent osteogenesis, osteoinduction, osteoconduction, and bacteriostasis. The osteogenic properties of the ZTA material for both surface functionalization methods were tested in vitro and linked to the surface chemistry through comparing the results obtained before and after surface functionalization, as shown in the Examples below.

The biomedical implant may be operable to be implanted in a patient's body in an area contacting or near bone. Non-limiting examples of biomedical implants include an intervertebral spinal implants, bone screws, spinal cages, orthopedic plates, wires, and other fixation devices, articulation devices in the spine, hip, knee, shoulder, ankle and phalanges, implants for facial or other reconstructive plastic surgery, middle ear implants, dental devices, and the like.

The biomedical implant or part of a biomedical implant may be made of a biocompatible material operable to be implanted in a patient for an extended period of time. In some examples, the biomedical implant may be formed from oxide ceramic materials, such as alumina, zirconia, zirconia-toughened alumina (ZTA), and the like. In at least one example, the biomedical implant may be a bulk or monolithic implant formed from ZTA. However, because oxide ceramic surfaces should not be directly exposed to bone tissue for long periods, the surface of the biomedical implant may be further functionalized using lasers and silicon nitride.

In an embodiment, the surface functionalization of the biomedical implant may include providing the biomedical implant, directing a laser to a surface of the biomedical implant to produce a plurality of patterned wells, and filling the patterned wells with a powder mixture of bioglass and silicon nitride.

The laser may be directed to the surface of the biomedical implant to generate a grid of equidistant, patterned wells.

The patterned wells may have a substantially cylindrical shape and/or a circular, oblong, square, or rectangular cross-section, or have any other two-dimensional feature extended into the surface of the biomedical implant. In various examples, the patterned wells may each have a diameter or size of at least about 100 μm, at least about 200 μm, at least about 300 μm, at least about 400 μm, at least about 500 μm, at least about 600 μm, at least about 700 μm, at least about 800 μm, or at least about 900 μm. In at least one example, the patterned wells each have a diameter of about 500 μm. In other examples, the patterned wells may have a cross-sectional area of about 0.01 mm², about 0.1 mm², about 0.2 mm², about 0.3 mm², about 0.4 mm², about 0.5 mm², or about 0.6 mm². The patterned wells may be regularly spaced, such that they have an interspace of about 0.5 mm, about 1.0 mm, about 1.5 mm, or about 2 mm. In at least one example, the patterned wells have an interspace of about 1 mm. The patterned wells may further form a grid. In some examples, the patterned wells are in a 4×4 grid.

In some examples, the laser may be a Nd:YAG laser. The laser may have a wavelength of 1064 nm, a focusing distance of about 250 mm, a nominal maximum power of about 17 kW, a burst energy of about 70 J, an applied potential of about 160-500 V, and/or a discharge time of about 1-20 ms.

The patterned wells may then be filled with a powder mixture of bioglass and silicon nitride. To form the powder mixture, powders of the bioglass and silicon nitride may first be homogenized and melted in a platinum crucible in nitrogen gas atmosphere. The melted mixture may then be quenched, before crushing the quenched mixture into fine powder to form the powder mixture. Filling the patterned wells may include pressing the powder mixture onto the biomedical implant surface, and removing the excess powder mixture.

In at least some examples, the bioglass is composed of 45 wt. % $SiO_2$, 24.5 wt. % CaO, 24.5 wt. % $Na_2O$, and 6 wt. % $P_2O_5$. In some examples, the silicon nitride is $\alpha$-$Si_3N_4$.

In some examples, the silicon nitride is present in the powder mixture at about 5 mol. %, about 6 mol. %, about 7 mol. %, about 8 mol. %, about 9 mol. %, or about 10 mol. %. Alternatively, the powder mixture may include at least about 5 wt. %, at least about 5.5 wt. %, at least about 6 wt. %, at least about 6.5 wt. %, at least about 7 wt. %, at least about 7.5 wt. %, at least about 8 wt. %, at least about 8.5 wt. %, at least about 9 wt. %, at least about 9.5 wt. %, at least about 10 wt. %, at least about 10.5 wt. %, or at least about 11 wt. % silicon nitride.

In another embodiment, the surface functionalization of the biomedical implant may include providing the biomedical implant, applying a layer of silicon nitride powder on a water-wet surface of the biomedical implant, pulsing a laser on the layer of silicon nitride to sinter the silicon nitride, and repeating the applying and pulsing steps until the sintered silicon nitride layer has a desired thickness.

In this embodiment, the silicon nitride may be $\beta$-$Si_3N_4$. In some examples, the silicon nitride is mixed with about 6 wt. % yttrium oxide and about 4 wt. % aluminum oxide.

In various examples, the desired thickness of silicon nitride sintered on the surface may be about 10 μm, about 15 μm, or about 20 μm.

In some examples, the laser is a Nd:YAG laser. The laser may have a wavelength of 1064 nm, a nominal maximum power of about 17 kW, a maximum pulse energy of about 70 J, a voltage of about 400 V, a spot size of about 2 μm, and/or a pulse time of about 4 ms.

Further provided herein is a method of promoting osteogenesis. The method may include contacting the biomedical implant with a silicon nitride surface functionalization with a tissue. In some examples, the tissue is bone tissue.

In some examples, osteoblast cell proliferation may increase on the biomedical implant as compared to an implant without a bioglass/silicon nitride powder mixture. In other examples, osteoblast cell proliferation may increase on the biomedical implant as compared to an implant without silicon nitride in the powder mixture. In some examples, area coverage and specific volume of biological tissue on the surface functionalized biomedical implant may be at least 200%, at least 225%, or at least 250% higher than that of an uncoated implant.

In additional examples, mineralized tissue increases on the biomedical implant as compared to an implant without a silicon nitride powder mixture. In at least one example, there is an increase in mineral hydroxyapatite on the biomedical implant as compared to an implant without the silicon nitride powder mixture.

Surprisingly, the poor osteogenic behavior of ZTA may be corrected by the surface functionalization methods described herein. Laser patterning and laser coating represent two distinct manufacturing approaches capable to limit the shortcomings of a direct contact between oxide surfaces and bone tissue. Without being limited to any particular theory, $Si_3N_4$ powder mixtures may stimulate the synthesis by osteoblasts of high-quality bone tissue, the former favoring bone matrix mineralization and the latter enhancing cell proliferation and formation of bone matrix. The left side of FIG. 10 shows a schematic of the interaction between $Si_3N_4$ and highly active osteoblasts. The corresponding upper part of the figure explicitly shows the cascade of off-stoichiometric equations governing the cell/$Si_3N_4$-substrate interactions in aqueous environment. The surface kinetics following $Si_3N_4$ hydrolysis indicates elution of $NR_4^+$/$NH_3$ ions and the formation of hydroxyl silanols. The availability of free electrons leads to decomposition of ammonia molecules with the formation of exogenous NO (used by the cells to signal further osteoblastogenesis) together with other RNS, while $NH_4^+$ enters the cytoplasmic space through specific channels as a nutrient. Note that exogenous RNS are also capable to cleave phosphate groups, thus supporting endogenous ALP in increasing phosphate concentration. Concurrently, the presence of silicic acid promotes osteogenesis.

$Al_2O_3$ and ZTA biomaterials have been recommended in the industry as components for dental and spinal fusion implants. However, based the interface chemistry and past clinical experiences with $Al_2O_3$-coated implants in the 1990s, a long-term protracted osteogenesis may not be achieved with implants made of ZTA ceramics. If ZTA materials are selected because of their long-term structural reliability, their surfaces should be functionalized in order to avoid a direct contact between cells and the implant surface. In this context, surface functionalization with $Si_3N_4$ is shown herein to produce osteogenic ZTA implants. Therefore, in some examples, an implant may be formed by functionalizing the surface of a ZTA implant with silicon nitride powder using a laser.

The osteogenic response of SaOS-2 cells was monitored on: (i) ZTA ceramic surfaces patterned with cylindrical wells before and after filling with Bioglass®/$Si_3N_4$ powder mixtures; and, (ii) ZTA surfaces coated with laser-sintered $Si_3N_4$. Statistically significant differences were found between the functionalized substrates and the pristine ZTA surface. Osteoblasts cultured on the pristine ZTA surface tended to become apoptotic due to the unfavorable surface chemistry of this material; accordingly, no osteogenic properties could be recognized for the ZTA surface. Surface patterning of the ZTA surface with a grid of cylindrical wells 500 µm in both diameter and depth did not by itself improve cell proliferation and osteogenesis. Filling the patterned wells with only Bioglass® increased the amount of mineralized apatite on the ZTA surface but had no impact on cell proliferation. Greatly enhanced osteoblast proliferation and a bone tissue with mineral/matrix ratio similar to that of human bones could be obtained by adding a 10 wt. % fraction $Si_3N_4$ to the Bioglass® mixture. Coating the ZTA surface with a layer of sintered $Si_3N_4$ greatly enhanced osteogenesis by directly translating to the ZTA surface the osteogenic properties of $Si_3N_4$ bioceramics.

Therefore, the surface chemistry of ZTA is unfriendly to osteoblasts, and should be regarded as unsuitable for implant applications in the human body that require long-term direct contact with bone tissue (e.g., dental implants and spine arthrodesis). However, surprisingly, functionalizing the ZTA surface by using $Si_3N_4$ or a mixture of Bioglass® and $Si_3N_4$ makes it bioactive and friendly to human prokaryotic cells.

EXAMPLES

Example 1: Surface Functionalization Procedures

ZTA samples (BIOLOX®delta, CeramTec, GmbH, Plochingen, Germany) were machined from 36 mm diameter femoral heads (year of production: 2014). The samples (10×10 mm with thickness of 3 mm) were cut using a slow-speed diamond coated blade and finely polished to a roughness on the order of the ten to twenty nanometers.
Laser-Patterning Procedure The device employed for laser-patterning the ZTA surface was a Vision LWI V ERGO-Workstation equipped with an Nd:YAG laser (wavelength of 1064 nm). Focusing distance, nominal maximum power, and burst energy were set at 250 mm, 17 kW, and 70 J, respectively, while the applied potential and discharge time were regulated in the range 160~500 V and 1~20 ms, respectively. The laser-patterning workstation was equipped with a gas nozzle connected to an Argon source at 1.2 atm to locally limit the presence of oxygen at the location of laser impingement. A motorized x-y stage with a precision of 10 µm was used to align the sample with the laser source and to produce a regular grid of equidistant wells 500 µm in diameter with an interspace of 1.0 mm.

Figure 1B:
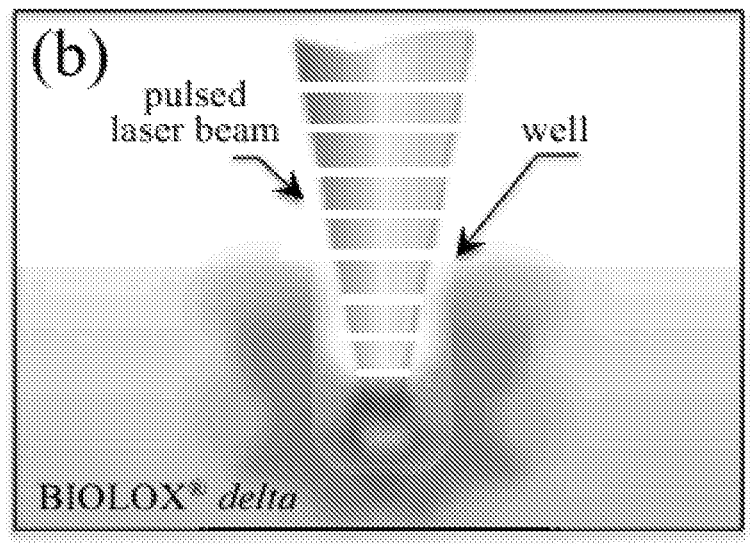
FIG. 1B is a schematic of a ZTA sample cross-section during laser excavation of a well according to the process depicted in FIG. 1A.
Figure 1C:
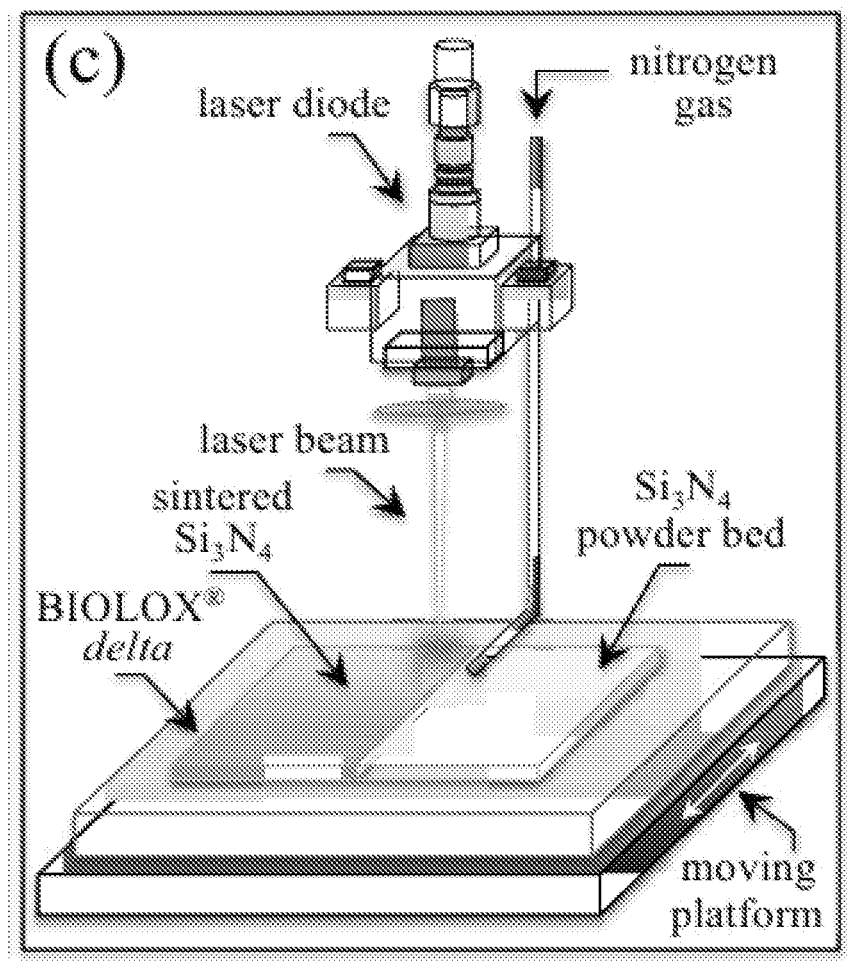
FIG. 1C shows deposition of a micrometer thick $Si_3N_4$ layer using an automatic 3D-additive laser-sintering procedure; and, FIG. 1D shows a cross section of the $Si_3N_4$ coating/laser interaction during the process depicted in FIG. 1C.
Figure 1D:
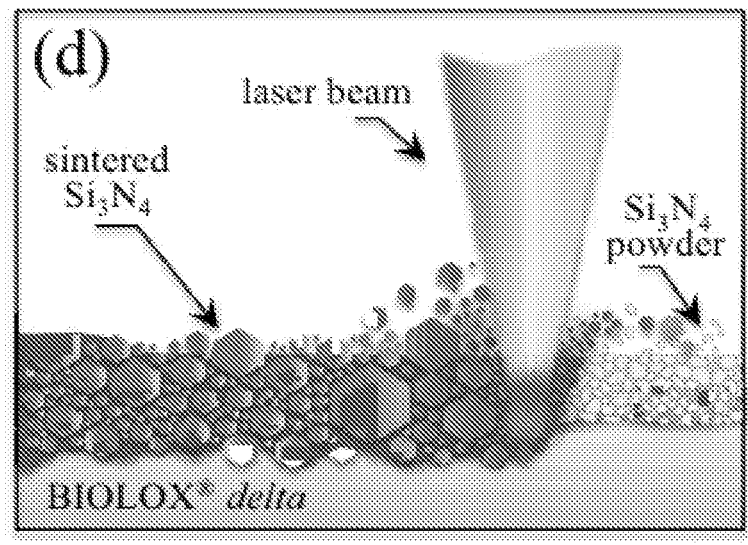

Standard 45S5 Bioglass® powder (Mo-Sci Corporation, Rolla, MO, USA) was used to fill the patterned wells. The composition in wt. % of the Bioglass® was as follows: 45% $SiO_2$, 24.5% CaO, 24.5% $Na_2O$, and 6% $P_2O_5$. The Bioglass® powder was mixed with 5 or 10 mol. % nm-sized $\alpha$-$Si_3N_4$ powder (SN-E10, Ube Co., Ube City, Japan). Powder mixtures of Bioglass® with 5 and 10 mol. % (corresponding to 5.51 and 10.69 wt. %) $\alpha$-$Si_3N_4$ were homogenized and melted in a platinum crucible in nitrogen gas atmosphere. After quenching, the melts were crushed into fine powder. Pure Bioglass® and Bioglass® mixtures with 5 and 10 wt. % $\alpha$-$Si_3N_4$ were used to fill the wells of different ZTA samples (n=6 for each type of filler). A schematic of the patterning and powder feeding procedures is shown in FIG. 1A. The sample cross-section during excavation of a cylindrical well on the ZTA surface by the pulsed laser beam is depicted in FIG. 1B.
Laser-Sintering Procedure The starting powder used for laser-sintering the $\alpha$-$Si_3N_4$ coating on the ZTA substrate consisted of $\beta$-$Si_3N_4$ (SINTX Co., Salt Lake City, UT, USA) mixed with 6 wt. % yttrium oxide ($Y_2O_3$, Grade C, H.C. Starck, Munich, Germany) and 4 wt. % aluminum oxide ($Al_2O_3$, SA8-DBM, Baikowski/Malakoff, Charlotte, North Carolina). The workstation and the Nd:YAG laser were the same as those described above. Successive layers of $Si_3N_4$ powder were placed on the water-wet surface of ZTA samples and the pulse laser repeatedly impinged to sinter/densify the coating. The conditions applied to achieve $Si_3N_4$-coating densification were the following: laser wavelength 1064 nm, max pulse energy: 70 joule, peak power 17 kW, voltage range 400 V, pulse time 4 ms, and spot size 2 µm. The apparatus operated under a constant flux of nitrogen gas flow in order to limit $Si_3N_4$ decomposition and oxidation. The operation was repeated until obtaining a homogeneous $\alpha$-$Si_3N_4$ coating with thickness, t=15±5 µm, over the entire surface of the ZTA substrate. A schematic of the overall laser-sintering procedure is depicted in FIG. 1C. The sample/laser interaction during sintering/densification of the $\alpha$-$Si_3N_4$ coating from the powder bed is shown in cross section in FIG. 1D.

Example 2: Methods of Surface Characterization

The surface morphology of the textured ZTA surface before and after filling with Bioglass®/$Si_3N_4$ powder mixtures was characterized with a confocal scanning laser microscope (Laser Microscope 3D and Profile measurements, Keyence, VKx200 Series, Osaka, Japan) capable of high-resolution optical images with depth selectivity. All images were collected using 20× magnification. Scanning Electron Microscopy (SEM) and Energy Dispersive X-ray Spectroscopy (EDS) (JSM-700 1F, JEOL, Tokyo, Japan) were used to acquire high-resolution images and chemical composition maps of $Si_3N_4$-coated substrates.

FTIR spectra were obtained using a high sensitivity spectroscope (Spectrum 100FT-IR Spotlight400; Perkin-Elmer Inc., Waltham, MA, USA). The spectral resolution of this equipment was 0.4 $cm^{-1}$. Average FTIR spectra were computed for each substrate from eight independent measurements. Pre-processing of raw data, which included baseline subtraction, smoothing, normalization, and fitting of the raw spectra, were performed using "R".

Example 3: Cell Culture and Biological Tests

SaOS-2 human osteosarcoma cells were cultured and incubated in 4.5 g/L glucose DMEM (D-glucose, L-Glutamine, Phenol Red, and Sodium Pyruvate; Nacalai Tesque, Kyoto, Japan) supplemented with 10% fetal bovine serum. The cells were then proliferated in petri dishes for 24 hours at 37° C. After adjusting the final cell concentration at $5\times10^5$ cell/ml, the cultured cells were deposited on the surface of $Si_3N_4$-coated and uncoated ZTA substrates (n=3 each type) previously sterilized by exposure to UV light. Osteoconductivity tests were conducted with seeding the cells in an osteogenic medium (DMEM supplemented with 50 µg/mL ascorbic acid, 10 mM $\beta$-glycerol phosphate, 100 mM hydrocortisone, and ~10% fetal bovine calf serum), and then incubating the samples for 7 days at 37° C. The medium was changed twice during the week of incubation.

Immunocytostaining was performed by fixing the SaOS-2 cells with 4% paraformaldehyde for 15 minutes and then incubating the samples for 30 minutes at room temperature with the following primary antibodies: mouse anti-human Gla osteocalcin (TakaraBio, Kusatsu-shi, Japan) and rabbit anti-human osteopontin (dilution=1:500) (IBL, Maebashi-Shi, Gunma, Japan). The cells were incubated with fluorescence conjugated and secondary antibodies Goat anti-Mouse Antibody FITC Conjugated (Bethyl Laboratories, Montgomery, TX, USA) and Goat anti-Rabbit Antibody PE Conjugated and (1:200) (Thermo Fisher Scientific, Waltham, MA, USA). Cell nuclei were stained with Hoechst33342 (1:100) (Dojindo, Kumamoto-Shi, Japan). The stained samples were observed under a fluorescence microscope (BZX710; Keyence, Osaka, Japan). Confocal scanning laser microscopy images were obtained with a 3D laser confocal microscope (OLS4000-SAT; Olympus Co., Tokyo, Japan) in order to assess the volumetric amounts per unit area of the bone tissue produced by the SaOS-2 cells after one-week exposure to the substrates. The amounts of osteocalcin and osteopontin in the deposited bony tissue were also estimated by direct pixel counting on fluorescence micrographs using automatic software.

Data relating to osteogenesis were analyzed by calculating their mean value±one standard deviation. The Student's t-test was used to detect statistically significant differences between data, p values<0.01 being considered statistically significant and labeled with an asterisk in the figures.

Example 4: Laser Patterned and Bioglass®/Si$_3$N$_4$-Filled ZTA Surfaces

Figure 3C:
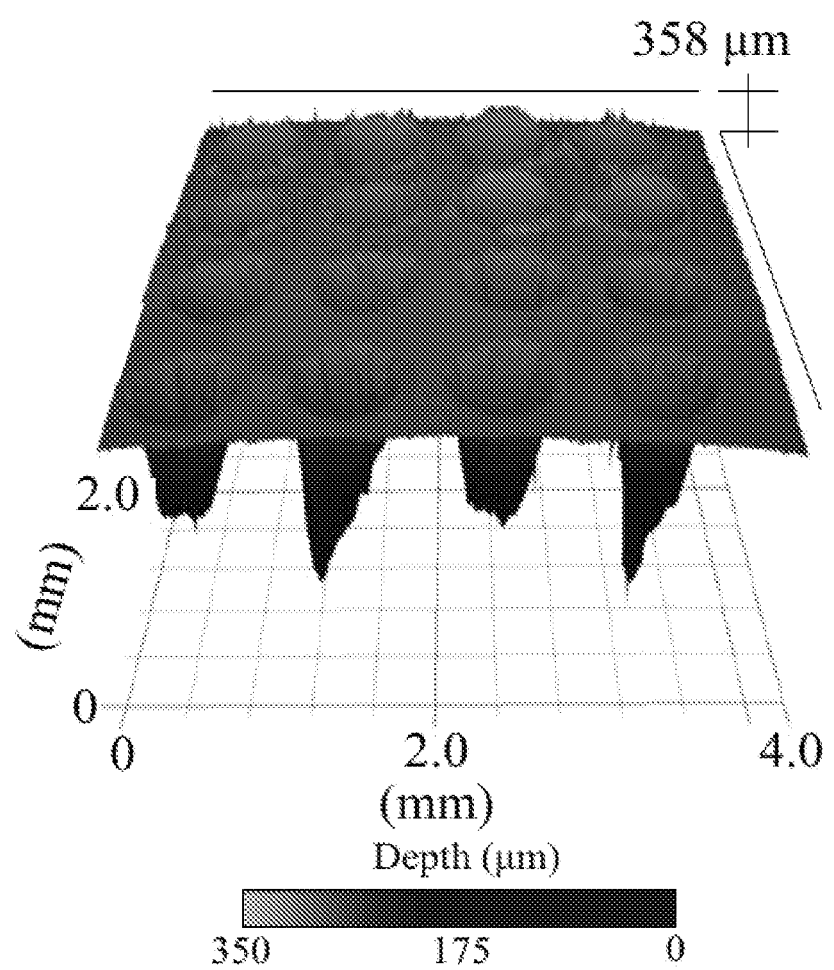
FIG. 3C is a three-dimensional laser microscopy characterization of the morphology of the wells.

FIGS. 2A and 2B show high-magnification images of a laser-drilled well on the ZTA surface as obtained by optical microscopy and laser topography, respectively. Similar images for the well after filling with Bioglass®/Si$_3$N$_4$ powder are shown in FIGS. 2C and 2D, respectively. Preliminary calibrations located the optimal conditions for patterning the ZTA surface. As seen from FIGS. 2A-2D, pulsed-laser drilling produced wells of a regular circular shape and with relatively sharp contours. Note, however, that ZTA partially melted under the laser beam and the molten material was ejected from the well producing some roughening in the neighborhood of the well border. Successive powder filling of the wells was then conducted. Filling of the laser-patterned wells was accomplished by first pressing the Bioglass®/Si$_3$N$_4$ powder mixtures onto the ZTA surface and then by manually removing the excess materials using a sharp blade. The powder mixture adhered to the internal walls of the wells. In this study, a diameter of 500 µm for the patterned wells was selected. This range of porosity is considered to be optimal for cell adhesion, proliferation, and stimulation of osteoblastic activity. FIGS. 3A and 3B show a 4×4 grid of wells 500 µm in diameter patterned on the ZTA surface as imaged by optical and laser scanning microscopes, respectively. An in-depth characterization of the morphology of the wells is shown in FIG. 3C. This latter characterization revealed a regular cylindrical shape for the wells with an irregular morphology for the bottom surface at depths comparable with the well diameter. Results of optical and laser microscopy showing Bioglass®/Si$_3$N$_4$ powder filling of the wells are given in FIGS. 3D and 3F, respectively. These latter observations showed that the wells were completely filled with the powder mixture.

Figure 4A:
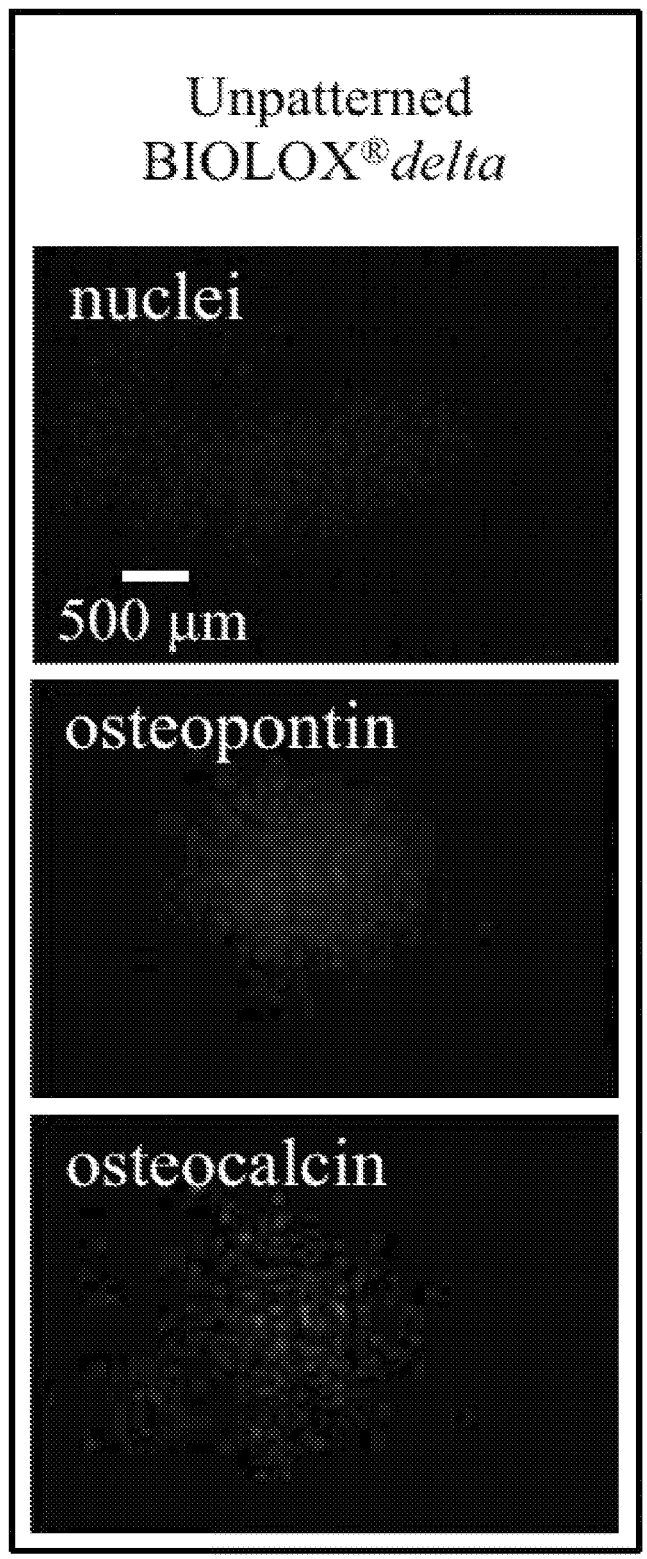
FIG. 4A shows fluorescence microscopy results on a pristine ZTA surface.
Figure 4B:
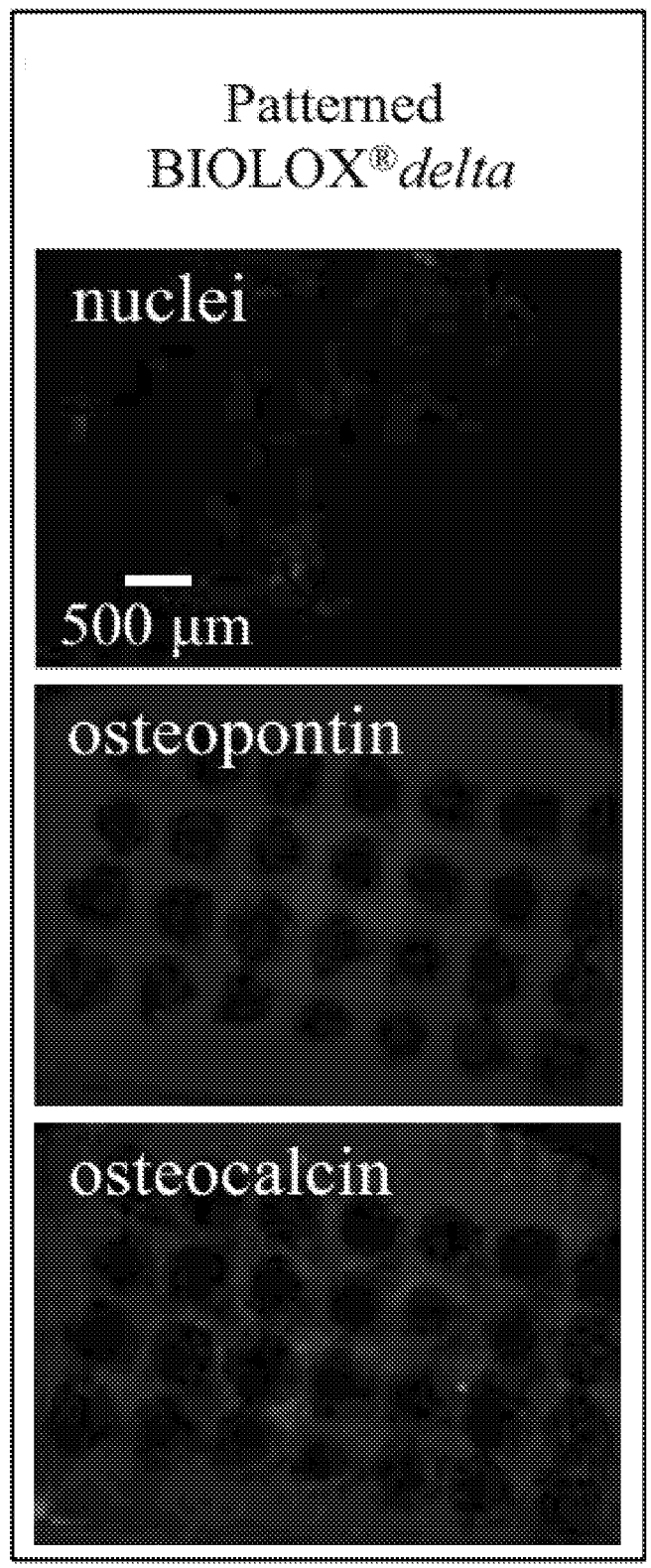
FIG. 4B shows fluorescence microscopy results on patterned ZTA.
Figure 4C:
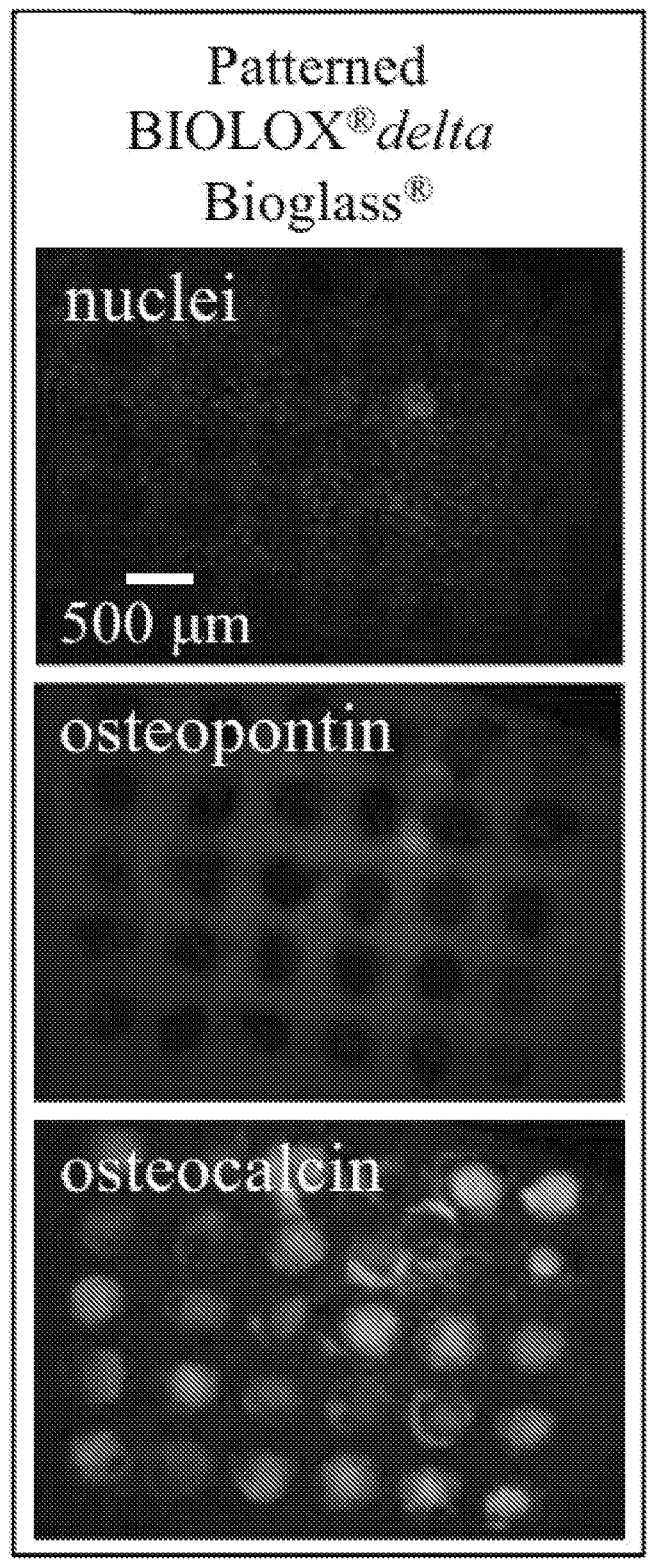
FIG. 4C shows fluorescence microscopy results on patterned ZTA surface filled with Bioglass® powder mixture.
Figure 4D:
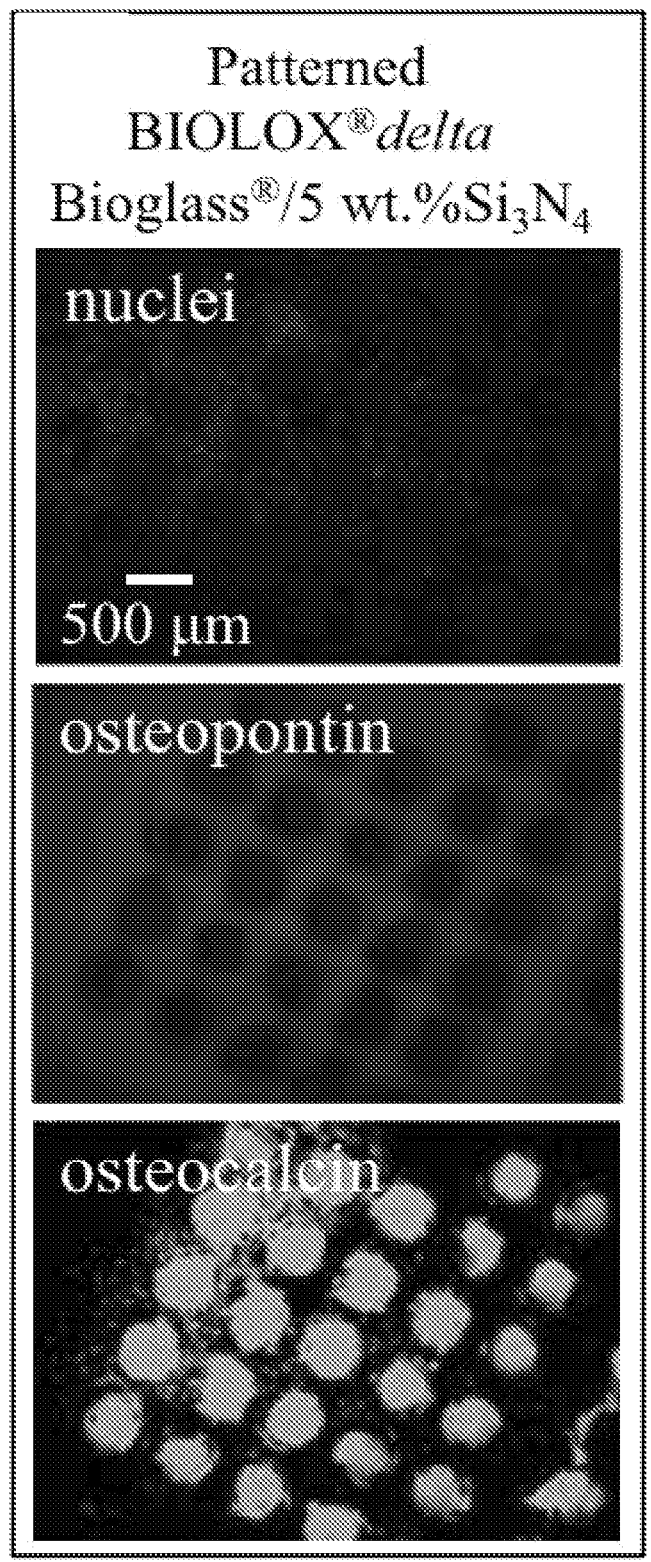
FIG. 4D shows fluorescence microscopy results on patterned ZTA filled with Bioglass®/5 wt. % $Si_3N_4$ powder mixture.
Figure 4E:
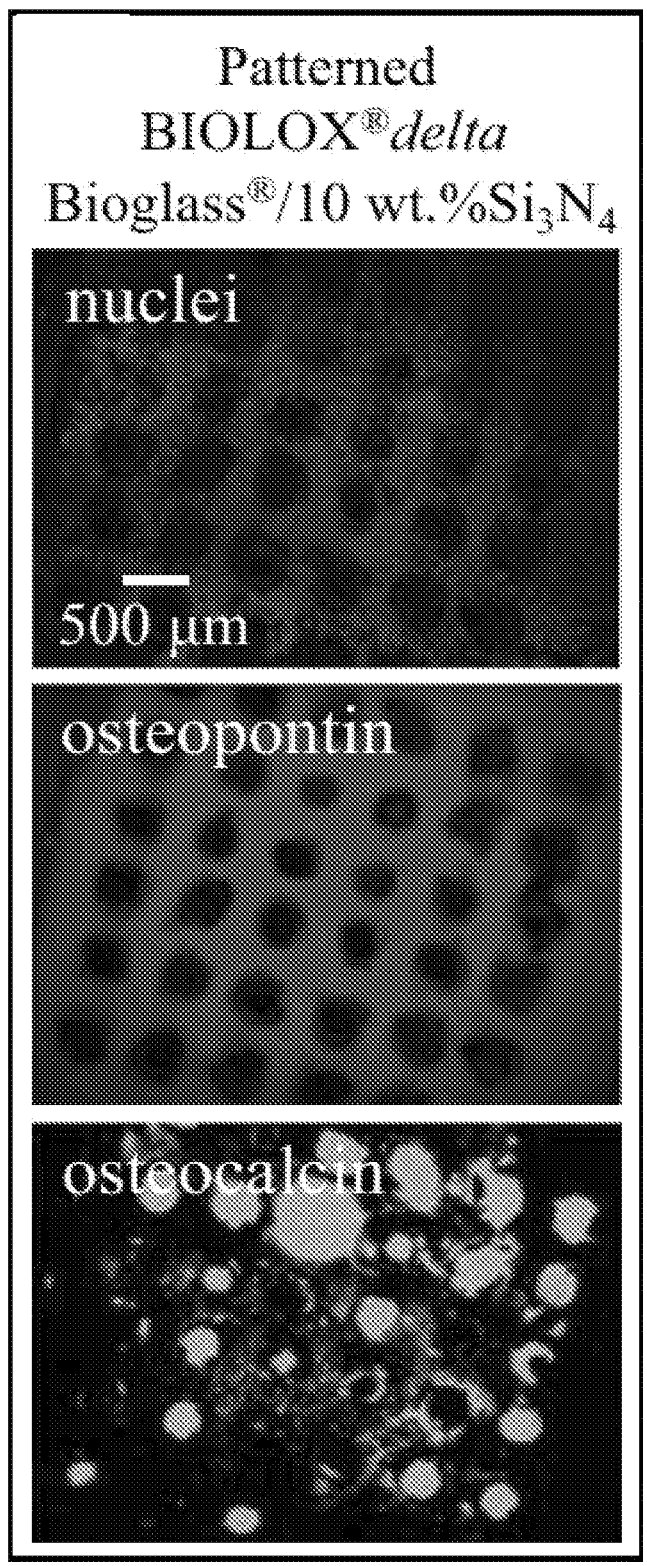
FIG. 4E shows fluorescence microscopy results on patterned ZTA filled with Bioglass®/10 wt. % $Si_3N_4$ powder mixture. The samples were exposed to SaOS-2 cells for 1 week.
Figure 5:
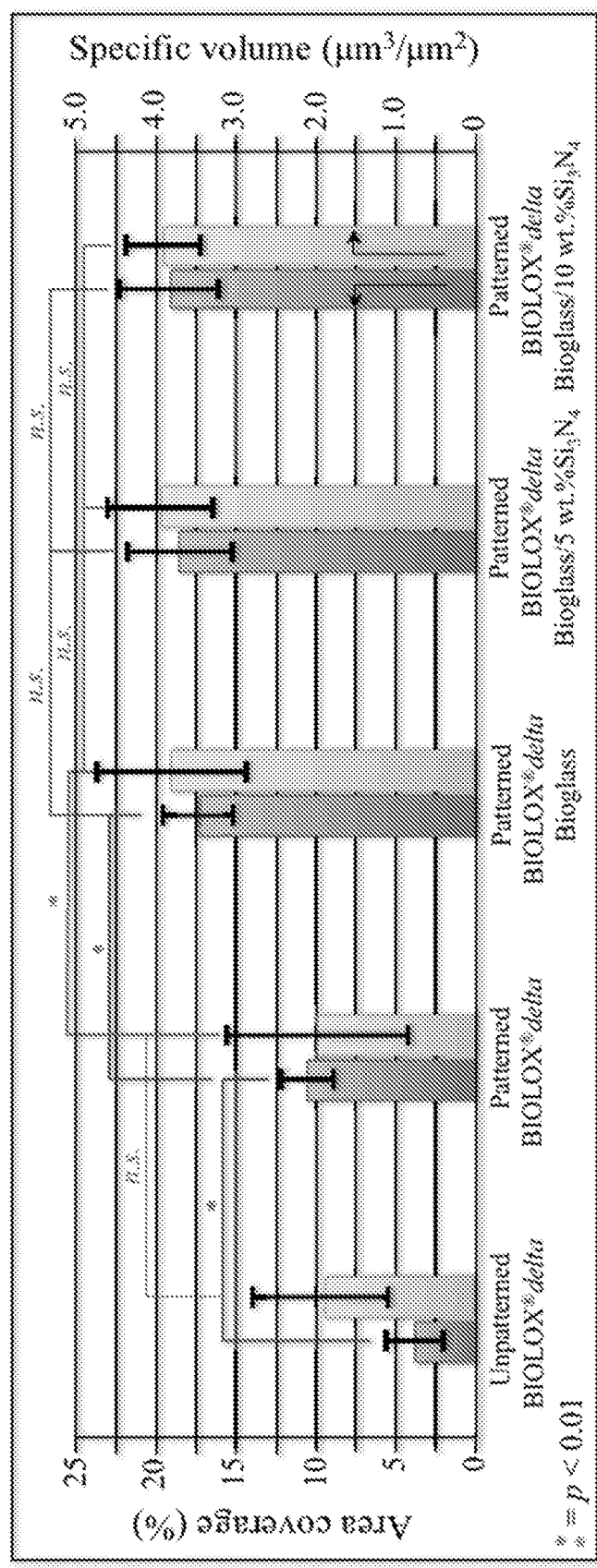
FIG. 5 shows quantitative laser microscopy data of area coverage and specific volume of biological tissue grown by osteoblasts on different substrates.
Figure 6A:
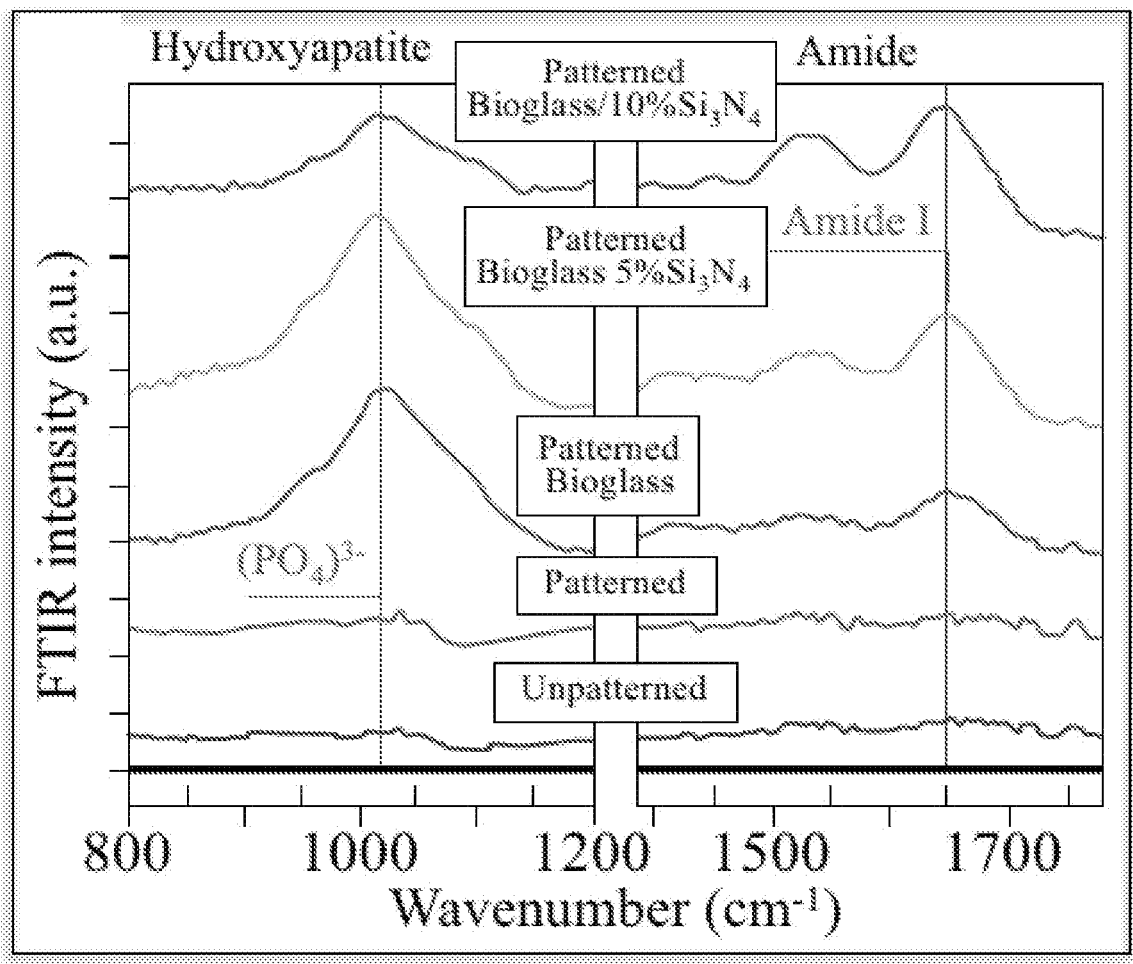
FIG. 6A shows results of FTIR characterizations on unpatterned, patterned, and patterned/filled ZTA samples (sample specifications in labels)
Figure 6B:
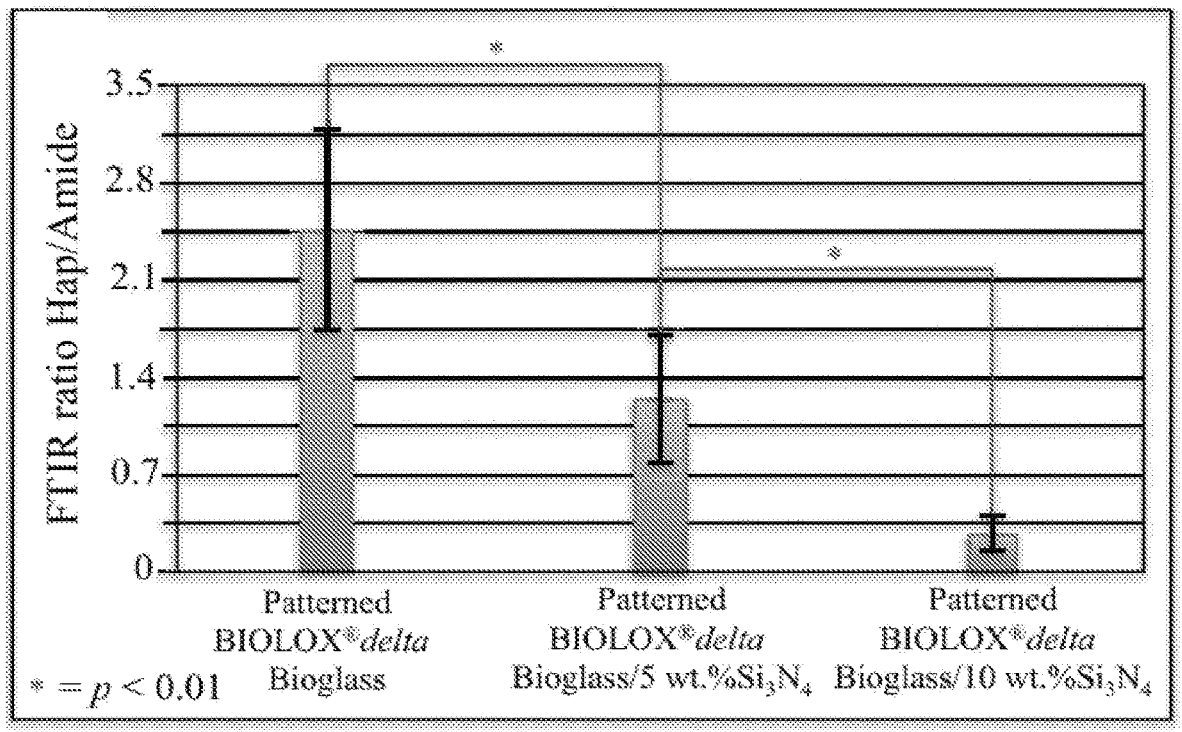
FIG. 6B is a plot of intensity ratios between apatite and organic matrix signals from FTIR spectra as a function of the type of ZTA substrate.

FIGS. 4A-4E shows the results of fluorescence microscopy from a (FIG. 4A) pristine ZTA surface, (FIG. 4B) patterned ZTA surface, (FIG. 4C) patterned ZTA surface filled with Bioglass® powder only, (FIG. 4D) patterned ZTA surface filled with Bioglass®/5 wt. % Si$_3$N$_4$ powder mixture, and (FIG. 4E) patterned ZTA surface filled with Bioglass®/10 wt. % Si$_3$N$_4$ powder mixture, after exposure to SaOS-2 cells for 1 week. Nuclei (blue), osteopontin (red), and osteocalcin (green) are tagged by fluorescence microscopy in the upper, middle, and bottom images of each section of FIGS. 4A-4E. After exposure to SaOS-2 cells for 1 week, the pristine ZTA substrate (FIG. 4A) showed no cell proliferation and only weak signals of osteocalcin and osteopontin, which indicates limited bioactive response to osteoblasts. Similarly, the patterned and unfilled ZTA sample (FIG. 4B) showed no cell proliferation and very weak osteocalcin/osteopontin signals within the wells and on flat regions. However, improvement in cell proliferation and osteocalcin/osteopontin were recorded for the patterned ZTA surfaces filled with Bioglass® (FIG. 4C). Greatly enhanced cell proliferation (blue signal) and osteopontin (red signal) were recorded on patterned ZTA surfaces filled with Bioglass®/Si$_3$N$_4$ mixtures; the higher the Si$_3$N$_4$ fraction in the powder mixture, the stronger the blue and red fluorescence signals (cf. FIGS. 4D and 4E). Moreover, the green osteocalcin fluorescence, which represented mineralized tissue regions, showed clear signals from the filled wells and also from the unpatterned regions of the ZTA surface when the wells were filled with Bioglass®/Si$_3$N$_4$ mixtures. FIG. 5 summarizes the quantitative data acquired by laser microscopy in terms of area coverage and specific volume of biological tissue grown by osteoblasts on different substrates. Both data sets were computed by excluding well areas to improve accuracy in comparing different samples, because those strongly fluorescent areas were of difficult evaluation. Area coverage and specific volume of biological tissue on ZTA patterned with Bioglass®/Si$_3$N$_4$ mixtures were ~200% and ~250% higher than that of unpatterned ZTA. There was no statistically significant difference among patterned ZTA samples filled with only Bioglass® and different Bioglass®/Si$_3$N$_4$ mixtures outside the well areas. However, the fluorescence images in FIGS. 4A-4E clearly show a strong increase in green fluorescence signals from the patterned ZTA surfaces when the powder mixture filling the wells included a fraction of Si$_3$N$_4$ powder. These data confirmed that the laser-patterning strategy greatly stimulated cell proliferation and biological tissue production. It should be noted that the addition of Bioglass® filler also stimulated the biological response. However, an increasing presence of Si$_3$N$_4$ in the powder mixture enhanced osteoblast proliferation (cf. FIGS. 4C and 4D) and fulfilled an important function in terms of bone quality. FIG. 6A shows the results of FTIR characterization on the full set of unpatterned, patterned, and patterned/filled ZTA samples. Two main results were extracted from the spectra: (i) addition of only Bioglass® filler led to a significant increase in signal intensity in the spectral region at around 1000 cm$^{-1}$, which represents mineral hydroxyapatite; and, (ii) addition of a fraction of Si$_3$N$_4$ to the Bioglass® filler led to an increase in relative intensity of signals at ~1500 cm$^{-1}$, which are associated with amides and represent the biological matrix of bone tissue. Consistent with the fluorescence data in FIGS. 4A-4E and their quantification in FIG. 5, no mineralized tissue was detected on either pristine or patterned ZTA surfaces. FIG. 6B gives a plot of intensity ratios between apatite and organic matrix signals in the FTIR spectra as a function of the type of ZTA substrate. Addition of only Bioglass® filler in the patterned wells caused a clear increase in intensity of mineral hydroxyapatite bands. However, the addition of 10 wt. % fraction of Si$_3$N$_4$ in the filler mixture brought the FTIR inorganic/organic band ratio of ZTA in the same range recorded for healthy bone tissue.

Example 5: Laser-Sintering of Si$_3$N$_4$-Coated ZTA Surfaces

Figure 7A:
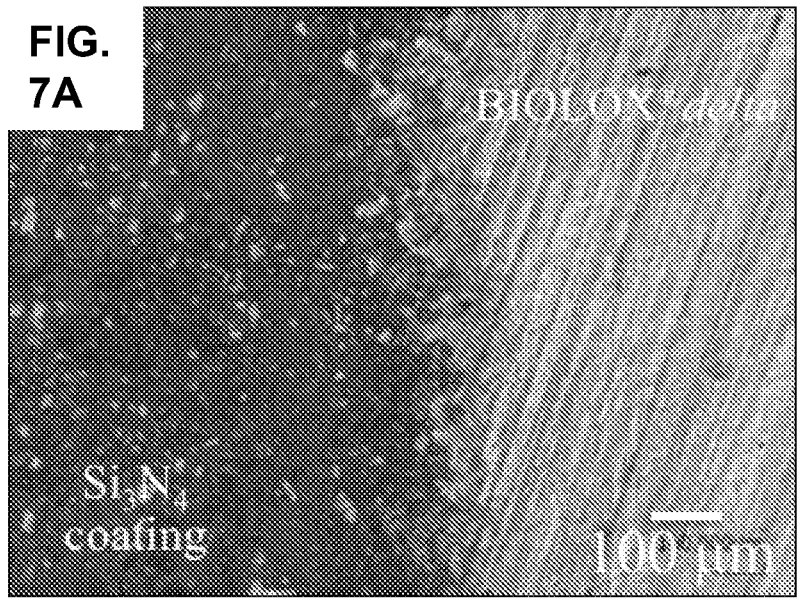
FIG. 7A is an optical micrographs take on the top surface of a partly $Si_3N_4$-coated BIOLOX®delta ZTA surface across the interface between coated and uncoated regions.
Figure 7B:
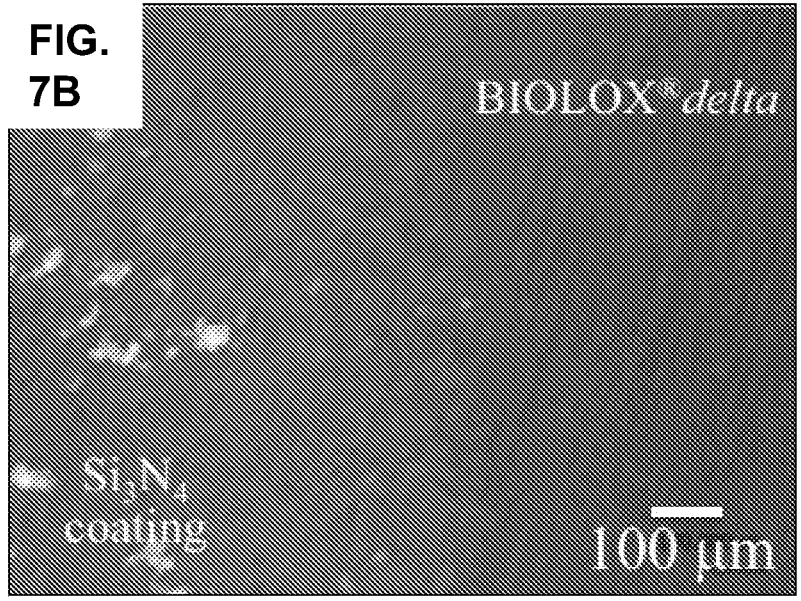
FIG. 7B is a laser micrograph taken on the top surface of a partly $Si_3N_4$-coated BIOLOX®delta ZTA surface across the interface between coated and uncoated regions.
Figure 7C:
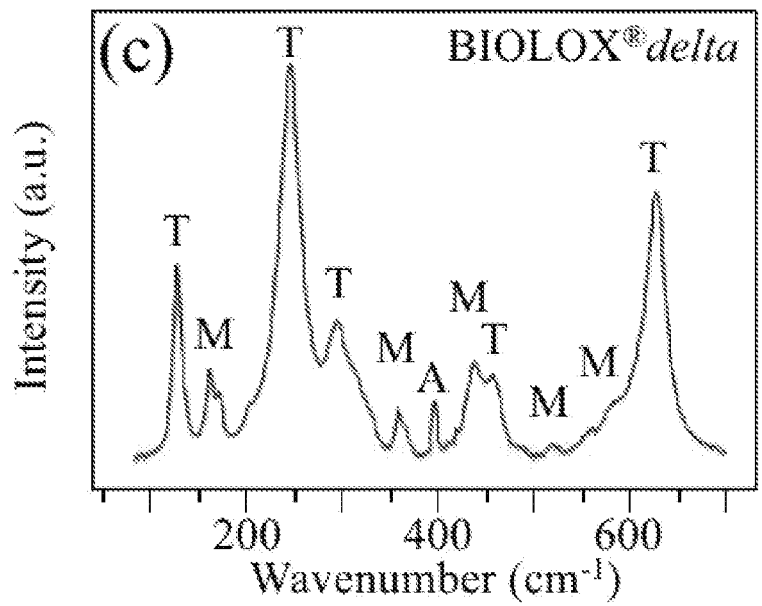
FIG. 7C shows Raman spectra collected on the ZTA uncoated side.
Figure 7D:
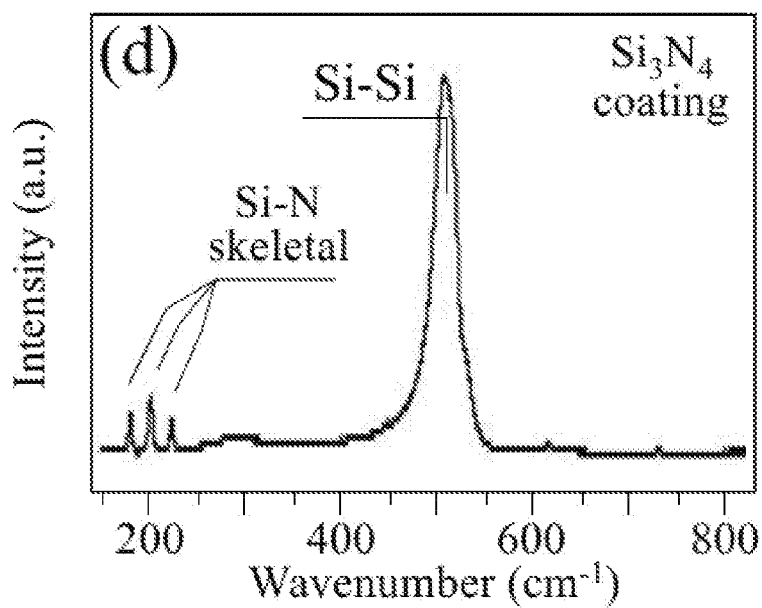
FIG. 7D shows Raman spectra collected on the $Si_3N_4$-coated side.

FIGS. 7A and 7B show optical and laser micrographs, respectively, taken on the top surface of a partly Si$_3$N$_4$- coated BIOLOX®delta ZTA surface across the interface between coated and uncoated regions (left and right sides of the micrographs, respectively). The three-dimensional view in FIG. 7B shows that the average thickness of the $Si_3N_4$ coating was in the order of t=15±5±m. The Raman spectra in the sections FIG. 7C and FIG. 7D were taken on the ZTA uncoated and $Si_3N_4$-coated sides, respectively. In FIG. 7C, the ZTA spectrum is composed of a number of bands which belong to the tetragonal and the monoclinic zirconia polymorphs (labeled as T and M, respectively) and one band from the alumina phase (at ~397 $cm^{-1}$; labeled A). Conversely, in the $Si_3N_4$-coated area, the Raman spectrum only presents the Si—N skeletal triplet at low frequencies and the Si—Si vibration band at ~510 $cm^{-1}$. This latter Raman band testifies the presence of free silicon clusters as a product of partial decomposition of the $Si_3N_4$ structure during laser sintering.

Figure 9A:
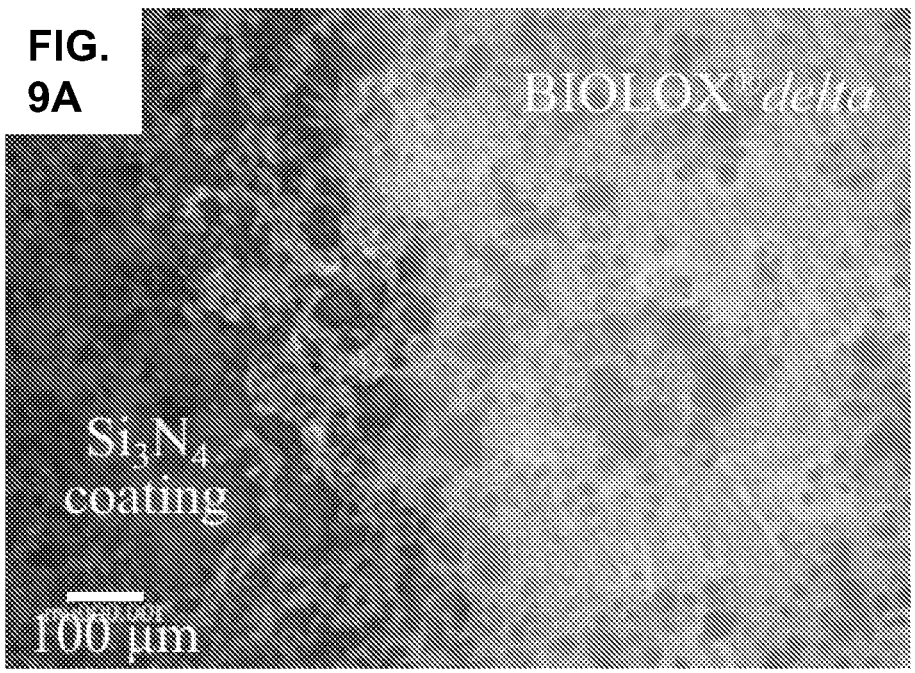
FIG. 9A is an optical micrograph of a large island of bone tissue grown by osteoblasts on the $Si_3N_4$-coated side of the BIOLOX®delta ZTA surface.
Figure 9B:
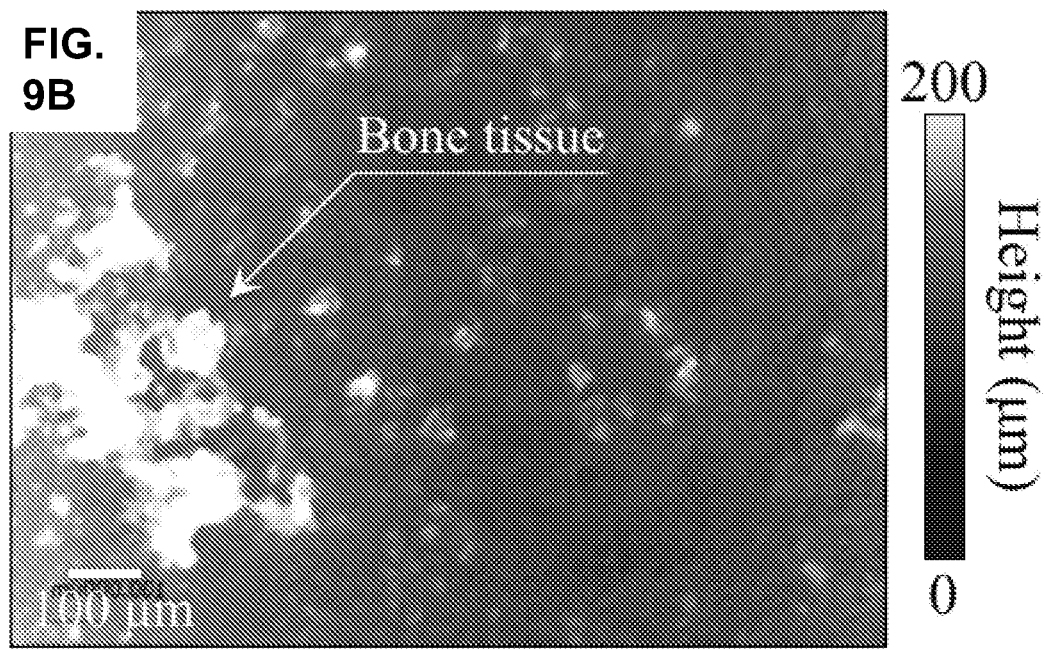
FIG. 9B is a laser micrograph of a large island of bone tissue grown by osteoblasts on the $Si_3N_4$-coated side of the BIOLOX®delta ZTA surface.
Figure 9C:
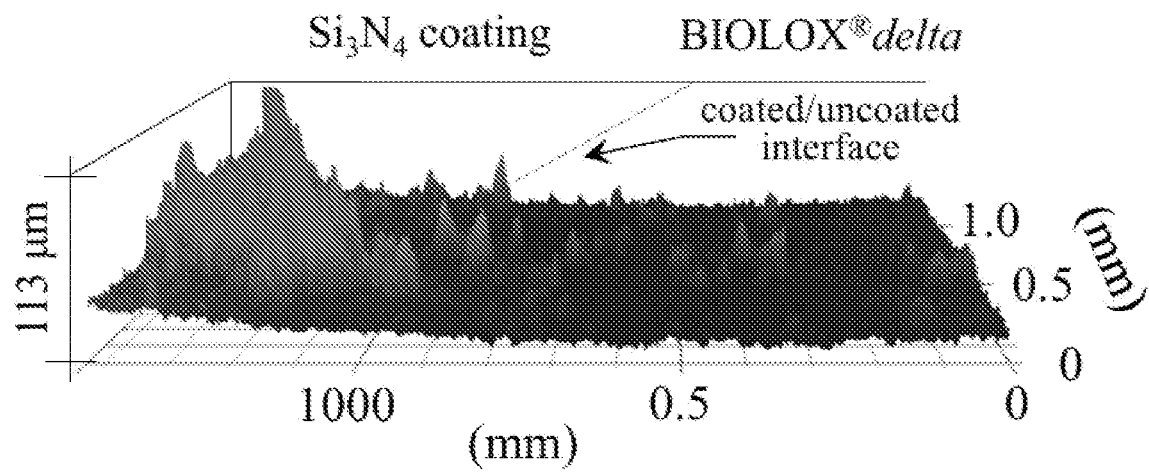
FIG. 9C is a three-dimensional laser microscopy view of the same island of bone tissue.
Figure 9D:
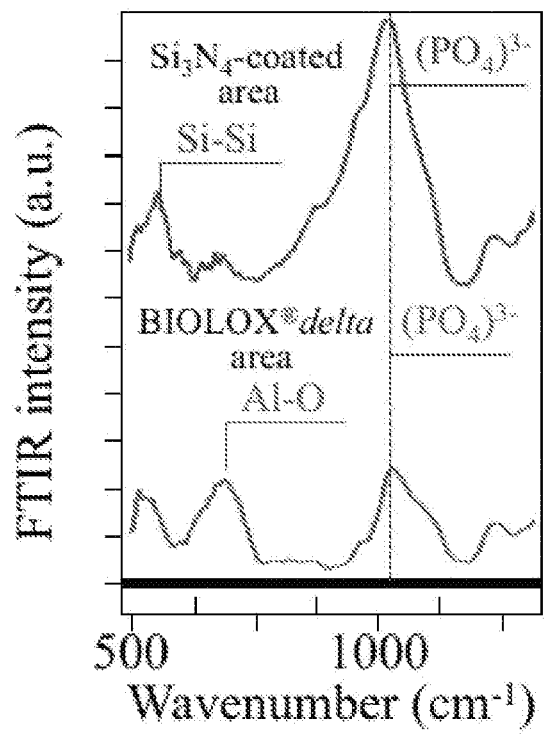
FIG. 9D is an average FTIR spectra collected in the neighborhood of the interface between $Si_3N_4$-coated and ZTA uncoated zones including the $(PO_4)^{3-}$ band of mineral apatite.

FIGS. 8A-8D shows SEM/EDS analyses performed on the same region in FIGS. 7A and 7B after 1-week in vitro exposure to SaOS-2 osteoblasts in biological environment. The main feature in the SEM micrograph in FIG. 8A is the presence of a thick coverage of bony apatite only on the left side of the micrographs (i.e., the part coated with $Si_3N_4$). EDS analyses of Si, Al, and Ca (in FIGS. 8B, 8C, and 8D, respectively) revealed Si-rich areas in coating area and no diffusional transport of the Al element into the coating during laser sintering (the very weak Al contamination in the coating area near the coated/uncoated interface, as seen in FIG. 8C, is believed to arise from melting residues created during laser processing). The presence of Si-rich areas corresponded to the presence of Ca from bony hydroxyapatite. Optical and laser micrographs of a large island of bone tissue grown by osteoblasts on the $Si_3N_4$-coated side of the BIOLOX®delta ZTA surface are shown in FIGS. 9A and 9B, respectively. The three-dimensional laser microscopy view in FIG. 9C reveals the details of the bone structure elevation reaching ~100 μm above the plane of the coated structure. Average FTIR spectra collected in the neighborhood of the interface between $Si_3N_4$-coated and ZTA uncoated zones (FIG. 9D) revealed a fourfold higher intensity of the $(PO_4)^{3-}$ band of mineral apatite in the former zone as compared to the latter. In sum, the consistency between EDS, laser microscopy, and FTIR data substantiates the positive effect of the $Si_3N_4$ coating toward enhancing the osteogenic performance of BIOLOX®delta ZTA ceramic versus human osteoblasts.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method of functionalizing the surface of a biomedical implant comprising:
   providing the biomedical implant;
   directing a laser to a surface of the biomedical implant, wherein the laser produces a grid of equidistant, patterned wells; and
   filling the grid of equidistant, patterned wells with a powder mixture comprising a bioglass and silicon nitride, wherein the silicon nitride is present in the powder mixture at about 5 mol. % to about 10 mol. %.

2. The method of claim 1, wherein the biomedical implant comprises zirconia-toughened alumina.

3. The method of claim 1, wherein the silicon nitride is α-$Si_3N_4$.

4. The method of claim 1, wherein the patterned wells comprise a two dimensional feature extended into the surface of the implant.

5. The method of claim 4, wherein the patterned wells are each about 0.2 $mm^2$ in cross-sectional area with an interspace of about 1.0 mm.

6. The method of claim 1, wherein the patterned wells are in a 4×4 grid.

7. The method of claim 1, wherein the bioglass comprises 45 wt. % $SiO_2$, 24.5 wt. % CaO, 24.5 wt. % $Na_2O$, and 6 wt. % $P_2O_5$.

8. The method of claim 1, wherein the powder mixture comprises 5.5 wt. % to about 10.7 wt. % silicon nitride.

9. The method of claim 1, wherein filling the patterned wells comprises:
   pressing the powder mixture onto the biomedical implant surface; and
   removing the excess powder mixture.

10. The method of claim 1 further comprising forming the powder mixture by:
    homogenizing and melting powder mixtures of the bioglass and silicon nitride in a platinum crucible in nitrogen gas atmosphere;
    quenching the melted mixture; and
    crushing the quenched mixture into fine powder.

11. The method of claim 1, wherein the laser is a Nd:YAG laser having a wavelength of 1064 nm.

12. The method of claim 1, wherein the laser has a focusing distance of about 250 mm, a nominal maximum power of about 17 kW, a burst energy of about 70 J, an applied potential of about 160-500 V, and/or a discharge time of about 1-20 ms.

13. A method of functionalizing the surface of a biomedical implant comprising:
    providing the biomedical implant;
    applying a layer of silicon nitride powder on a water-wet surface of the biomedical implant;
    pulsing a laser on the layer of silicon nitride to sinter the silicon nitride; and
    repeating the applying and pulsing steps until the sintered silicon nitride layer has a thickness of about 10 μm to about 20 μm.

14. The method of claim 13, wherein the biomedical implant comprises zirconia-toughened alumina.

15. The method of claim 13, wherein the silicon nitride is β-$Si_3N_4$.

16. The method of claim 15, wherein the silicon nitride is mixed with 6 wt. % yttrium oxide and 4 wt. % aluminum oxide.

17. The method of claim 13, wherein the laser is a Nd:YAG laser having a wavelength of 1064 nm.

18. The method of claim 13, wherein the laser has a nominal maximum power of about 17 KW, a maximum pulse energy of about 70 J, a voltage of about 400 V, a spot size of about 2 μm, and/or a pulse time of about 4 ms.

\* \* \* \* \*